(12) United States Patent
Benson et al.

(10) Patent No.: US 8,252,826 B2
(45) Date of Patent: *Aug. 28, 2012

(54) CYCLOPENTYL- AND CYCLOHEPTYLPYRAZOLES

(75) Inventors: Gregory Martin Benson, Therwil (CH); Konrad Bleicher, Freiburg (DE); Uwe Grether, Efringen-Kirchen (DE); Bernd Kuhn, Reinach BL (CH); Hans Richter, Grenzach-Wyhlen (DE); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/050,031

(22) Filed: Mar. 17, 2011

(65) Prior Publication Data

US 2011/0237628 A1  Sep. 29, 2011

(30) Foreign Application Priority Data

Mar. 24, 2010  (EP) .................................... 10157484

(51) Int. Cl.
- *A61K 31/41* (2006.01)
- *A61K 31/415* (2006.01)
- *C07D 257/02* (2006.01)
- *C07D 231/10* (2006.01)

(52) U.S. Cl. ...... 514/381; 514/406; 548/252; 548/356.1
(58) Field of Classification Search .................. 514/381, 514/406; 548/252, 356.1
See application file for complete search history.

(56) References Cited

U.S. PATENT DOCUMENTS

| 8,008,505 B2 | 8/2011 | Benson et al. |
| 2007/0093540 A1 | 4/2007 | Allegrini et al. |
| 2009/0197886 A1 | 8/2009 | Liotta et al. |
| 2010/0076027 A1 | 3/2010 | Benson et al. |

FOREIGN PATENT DOCUMENTS

| JP | 2001/064176 | 3/2001 |
| WO | 2007/052843 | 5/2007 |
| WO | 2007052843 | 5/2007 |
| WO | 2007/140174 | 12/2007 |
| WO | 2007/140183 | 12/2007 |
| WO | 2010/034649 | 4/2010 |

OTHER PUBLICATIONS

Office Action mailed Aug. 17, 2010 in co-pending U.S. Appl. No. 12/563,193 now US Patent No. 8,008,505—Issued: Aug. 30, 2011.
Liu et al., "Heterocycles" 71:1755-1763 ( 2007).
Datta et al., "J. Biol. Chem." 281:807-812 ( 2006).
Domazon et al., "Journal of Heterocyclic Chemistry" (XP002560056), 19:117-121 ( 1982).
Kast et al., "J. Biol. Chem." 277:2908-2915 ( 2002).
Makishima et al., "Science" 284:1362-1365 ( 1999).
Liu et al., "J. Clin. Invest." 112:1678-1687 ( 2003).
Sinal et al., "Cell" 102:731-744 ( 2000).
Office Action mailed Oct. 13, 2010 in co-pending U.S. Appl. No. 12/563,193 now US Patent No. 8,008,505—Issued: Aug. 30, 2011.
Ananthanarayanan et al., "J. Biol. Chem." 276:28857-28865 ( 2001).
Makishima et al., "Mol. Cell" 6:507-515 ( 2000).
Ramachandran et al., "Tetrahedron Asymmetry" 5:1061-1074 ( 1994).
Corey et al., "J. Am. Chem. Soc." 109:5551-5553 ( 1987).
Zhang et al., "Tetrahedron Letters" 47:7641-7644 ( 2006).
Shirtcliff et al., "J. Org. Chem." 71:6619-6622 ( 2006).
PCT International Search Report dated May 30, 2011 PCT/EP2011/054176.
Luga et al., "Pesticide Science" 42:29-36 ( 1994).
Hazeldine et al., "Chem." 13:3910-3920 ( 2005).
Grieder et al., "Synthesis" 11:1707-1711 ( 2003).

*Primary Examiner* — Rebecca Anderson
*Assistant Examiner* — Samantha Shterengarts
(74) *Attorney, Agent, or Firm* — George W. Johnston; Patricia S. Rocha-Tramaloni; Gene J. Yao

(57) ABSTRACT

This invention relates to novel cyclopentyl- and cycloheptylpyrazole derivatives of the formula I

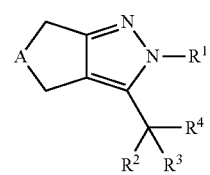

wherein A and $R^1$ to $R^4$ are as defined in the description and in the claims, as well as physiologically acceptable salts thereof. The invention relates also to compositions including these compounds and methods of using the compounds.

17 Claims, No Drawings

CYCLOPENTYL- AND CYCLOHEPTYLPYRAZOLES

PRIORITY TO RELATED APPLICATION(S)

This application claims the benefit of European Patent Application No. 10157484.6 filed Mar. 24, 2010, which is hereby incorporated by reference in its entirety.

FIELD OF THE INVENTION

The present invention relates to novel cyclopentyl- and cycloheptylpyrazoles useful in the treatment or prophylaxis of diseases which are affected by FXR modulators, and in particular useful for treating dyslipidemia.

In particular, the present invention is concerned with novel cyclopentyl- and cycloheptylpyrazole derivatives of the formula

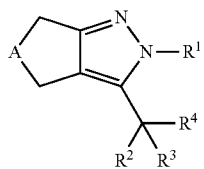

wherein A is $-CH_2-$ or $-(CH_2)_3-$, and $R^1$ to $R^4$ are defined herein below, or pharmaceutically acceptable salts thereof, their manufacture, pharmaceutical compositions containing them, methods of using them and their use as medicaments for the treatment of diseases which are affected by FXR modulators.

The compounds are selective modulators of the farnesoid-X-receptor, in particular agonists of the farnesoid-X-receptor.

BACKGROUND OF THE INVENTION

The farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. (1999) Identification of a nuclear receptor for bile acids. Science 284, 1362-5]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXR alpha and blocks their transcriptional functions [Lu, T. T., Makishima, M., Repa, J. J., Schoonjans, K., Kerr, T. A., Auwerx, J. and Mangelsdorf, D. J. (2000) Molecular basis for feedback regulation of bile acid synthesis by nuclear receptors. Mol Cell 6, 507-15]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tan, P. T., Jones, S. A., Anisfeld, A. M., Stoltz, C. M., Tontonoz, P., Kliewer, S., Willson, T. M. and Edwards, P. A. (2002) Regulation of multidrug resistance-associated protein 2 (ABCC2) by the nuclear receptors pregnane X receptor, farnesoid X-activated receptor, and constitutive androstane receptor. J Biol Chem 277, 2908-15; Ananthanarayanan, M., Balasubramanian, N., Makishima, M., Mangelsdorf, D. J. and Suchy, F. J. (2001) Human bile salt export pump promoter is transactivated by the farnesoid X receptor/bile acid receptor. J Biol Chem 276, 28857-65]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. (2003) Hepatoprotection by the farnesoid X receptor agonist GW4064 in rat models of intra- and extrahepatic cholestasis. J Clin Invest 112, 1678-87; Sinal, C. J., Tohkin, M., Miyata, M., Ward, J. M., Lambert, G. and Gonzalez, F. J. (2000) Targeted disruption of the nuclear receptor FXR/BAR impairs bile acid and lipid homeostasis. Cell 102, 731-44]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. (2006) Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. J Biol Chem 281, 807-12]. FXR also decreases hepatic synthesis of triglycerides by repressing SREBP1-c expression by an alternate pathway involving SHP and LXRalpha. Thus compounds which modulate FXR activity may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol >240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple co-morbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g. methyl, ethyl, n-propyl, isopropyl, n-butyl, s-butyl, t-butyl, pentyl, 1,1,3,3-tetramethyl-butyl and the like. In particular, the term "alkyl" includes lower alkyl groups as described below.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, particularly methyl and ethyl and most particularly methyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. In particular, the term "cycloalkyl" means cyclohexyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. An example is cyclopropyl-methyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, particularly methoxy and ethoxy.

The term "cycloalkyloxy" or "$C_{3-7}$-cycloalkyloxy" refers to the group R"—O—, wherein R" is cycloalkyl. Examples of cycloalkyloxy groups are cyclopropyloxy, cyclobutyloxy, cyclopentyloxy, cyclohexyloxy and cycloheptyloxy.

The term "alkoxycycloalkyl" denotes the saturated $C_{3-7}$-cycloalkyl group as defined above, however one of 3 to 7 carbon atoms is replaced by an O atom. Examples of "alkoxycycloalkyl" groups are oxirane, oxetane, tetrahydrofuran and tetrahydropyrane, in particular oxirane.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, more particularly fluoro. Among the halogenated lower alkyl groups are trifluoromethyl, difluoromethyl, trifluoroethyl, 2,2-difluoroethyl, fluoromethyl and chloromethyl.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, more particularly fluoro. Among the preferred halogenated lower alkoxy groups are trifluoromethoxy, difluoromethoxy, fluormethoxy and chloromethoxy.

The term "carboxyl" means the group —COOH.

The term "lower alkoxycarbonyl" or "$C_{1-7}$-alkoxycarbonyl" refers to the group —CO—OR' wherein R' is lower alkyl and the term "lower alkyl" has the previously given significance. Examples for lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. An example for a lower alkoxycarbonylalkyl group is —CH$_2$—COOCH$_3$.

The term "lower alkoxycarbonylalkoxy" or "$C_{1-7}$-alkoxycarbonyl-$C_{1-7}$-alkoxy" refers to lower alkoxy groups as defined above wherein one of the hydrogen atoms of the lower alkoxy group is replaced by $C_{1-7}$-alkoxycarbonyl. An example for a lower alkoxycarbonylalkoxy group is t-butoxycarbonylmethoxy (xO—CH$_2$—COO—C(CH$_3$)$_3$).

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxyl alkyl groups are carboxylmethyl (—CH$_2$—COOH) and carboxylethyl (—CH$_2$—CH$_2$—COOH), in particular carboxylmethyl.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. An example for a lower carboxylalkoxy group is carboxylmethoxy (—O—CH$_2$—COOH).

The term "heterocyclyl" refers to 5 to 6 membered monocyclic ring or 8 to 10 membered bi- or tricyclic ring which can comprise 1, 2 or 3 atoms selected from nitrogen, oxygen and/or sulphur, such as morpholinyl, thiomorpholinyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl, piperazinyl, tetrahydrofuranyl and tetrahydropyranyl. In particular, the term "heterocyclyl" refers to tetrahydrofuranyl and tetrahydropyranyl.

The term "protecting group" refers to groups which are used to protect functional groups, particularly hydroxy groups, temporarily. Typical examples of protecting groups are benzyl, p-methoxybenzyl, t-butyl-dimethylsilyl, t-butyl-diphenylsilyl and (for protection of amino groups) Boc and benzyloxycarbonyl.

Compounds of formula I can form pharmaceutically acceptable salts. Examples of such pharmaceutically acceptable salts are acid addition salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I in which a COOH group is present can further form salts with bases. Examples of such salts are alkaline, earth-alkaline and ammonium salts such as e.g. Na-, K-, Ca- and trimethylammoniumsalt. The term "pharmaceutically acceptable salts" also refers to such salts.

In detail, the present invention provides compounds of the formula

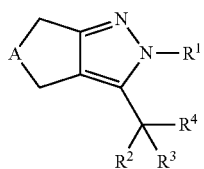

I wherein
A is —CH$_2$— or —(CH$_2$)$_3$—,
R$^1$ is a ring selected from phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;
R$^2$ is selected from the group consisting of hydrogen, methyl, ethyl, hydroxy, methoxy, fluoro, fluoromethyl, difluoromethyl and trifluoromethyl;
R$^3$ is selected from the group consisting of:
unsubstituted cycloalkyl;
cycloalkyl substituted 1 to 4 groups independently selected from methyl and fluoro, lower cycloalkylalkyl;
unsubstituted phenyl;
phenyl substituted with 1 to 3 substituents independently selected from the group consisting of lower alkyl, halogen, lower halogenalkyl, hydroxy, lower alkoxy, lower halogenalkoxy and cyano; and
heterocyclyl;
R$^4$ is selected from the group consisting of —C(O)—NH—R$^5$, —CR$^7$R$^8$—OR$^6$, —O—(CR$^7$R$^8$)$_n$—R$^6$;
—CR$^7$R$^8$—SR$^6$, —CR$^7$R$^8$—SO—R$^6$, —CR$^7$R$^8$—SO$_2$—R$^6$,
—CR$^7$R$^8$—NH—R$^6$; —CH═CH—R$^6$ and —(CH$_2$)$_2$—R$^6$,
wherein
n is 0 or 1,
R$^5$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
unsubstituted phenyl;
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl and tetrazolyl;
R$^6$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl;
unsubstituted pyridyl;
pyridyl substituted by carboxyl, lower alkoxycarbonyl or tetrazolyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and
R$^7$ and R$^8$ independently are selected from the group consisting of hydrogen, lower alkyl and lower halogenalkyl, or
R$^7$ and R$^8$ together with the carbon atom to which they are attached form a cycloalkyl or alkoxycycloalkyl ring;
or a pharmaceutically acceptable salt thereof.

The invention provides compounds of formula I, wherein R$^1$ is a ring selected from phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano. The invention thus also provides compounds of formula I, wherein R$^1$ is a phenyl ring, said ring being unsubstituted or substituted with 1 to 3 substituents independently selected from the group consisting of lower alkyl, halogen, lower halogenalkyl, hydroxy, lower alkoxy, lower halogenalkoxy and cyano. Specifically, the invention provides compounds of formula I, wherein R$^1$ is phenyl or phenyl substituted with halogen.

Compounds of formula I according to the invention are further those, wherein R$^2$ is selected from the group consisting of hydrogen, methyl, ethyl, hydroxy, methoxy, fluoro, fluoromethyl, difluoromethyl and trifluoromethyl. The invention also provides compounds of formula I, wherein $R^2$ is hydrogen.

Furthermore, compounds of formula I according to the invention are those, wherein $R^3$ is selected from the group consisting of:
unsubstituted cycloalkyl or cycloalkyl substituted 1 to 4 groups independently selected from methyl and fluoro;
lower cycloalkylalkyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy and cyano; and
heterocyclyl.

The invention also relates to compounds of formula I, wherein $R^3$ is cycloalkyl.

A particular group of compounds of the present invention are those, wherein $R^4$ is selected from the group consisting of —C(O)—NH—$R^5$, —$CR^7R^8$—$OR^6$ and —$CR^7R^8$—$SR^6$, wherein $R^5$ is selected from the group consisting of
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
unsubstituted phenyl;
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl or tetrazolyl;
$R^6$ is selected from the group consisting of
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
heterocyclyl;
unsubstituted pyridyl;
pyridyl substituted by carboxyl, lower alkoxycarbonyl or tetrazolyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and
$R^7$ and $R^8$ independently are selected from the group consisting of hydrogen, lower alkyl and lower halogenalkyl, or
$R^7$ and $R^8$ together with the carbon atom to which they are attached form a cycloalkyl or alkoxycycloalkyl ring.

The invention thus provides compounds of formula I, wherein $R^4$ is —C(O)—NH—$R^5$; and
$R^5$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
unsubstituted phenyl;
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl and tetrazolyl.

More specifically, the invention provides compounds, wherein $R^4$ is —C(O)—NH—$R^5$ and $R^5$ is selected from the group consisting of:
cycloalkyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl.

The invention thus also provides compounds of formula I, wherein $R^4$ is —C(O)—NH—$R^5$ and $R^5$ is selected from the group consisting of: cycloalkyl and phenyl substituted with 1 to 3 substituents independently selected from the group consisting of lower alkyl, halogen, carboxyl, tetrazolyl, lower alkoxycarbonyl, lower carboxylalkoxy, lower alkoxycarbonylalkoxy and cyano.

The invention further provides compounds of formula I, wherein $R^4$ is —C(O)—NH—$R^5$ and $R^5$ is cycloalkyl or phenyl substituted with 1 to 3 substituents independently selected from the group consisting of halogen, carboxyl, lower alkoxycarbonyl, lower carboxylalkoxy and lower alkoxycarbonylalkoxy.

Also provided are compounds of formula I according to any one of claims 1 to 6, wherein $R^4$ is —$CR^7R^8$—$OR^6$ and wherein
$R^6$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
heterocyclyl;
unsubstituted pyridyl;
pyridyl substituted by carboxyl, lower alkoxycarbonyl or tetrazolyl;
unsubstituted phenyl; and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and $R^7$ and $R^8$ are hydrogen.

More specifically, the invention provides compounds of formula I, wherein $R^4$ is —$CR^7R^8$—$OR^6$, $R^6$ is selected from the group consisting of cycloalkyl and phenyl substituted with 1 to 3 substituents independently selected from the group consisting of lower alkyl, halogen, carboxyl, tetrazolyl, lower alkoxycarbonyl, lower carboxylalkoxy, lower alkoxycarbonylalkoxy and cyano, and $R^7$ and $R^8$ are hydrogen.

The invention further provides compounds of formula I, wherein A is —$CH_2$—. These are compounds having the formula I-I

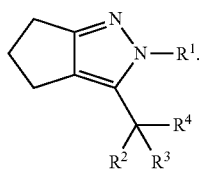

The invention also provides compounds of formula I, wherein A is —$(CH_2)_3$—. These are compounds having the formula I-II

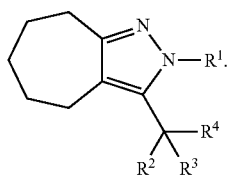

The invention further relates to compounds of formula I that are selected from the group consisting of
4-{2-[2-(4-chloro-phenyl)-2,4,5,6-tetrahydro-cyclopentapyrazol-3-yl]-2-cyclohexyl-ethoxy}-3,5-dimethyl-benzoic acid methyl ester,
4-{2-[2-(4-chloro-phenyl)-2,4,5,6-tetrahydro-cyclopentapyrazol-3-yl]-2-cyclohexyl-ethoxy}-3,5-dimethyl-benzoic acid,
4-{2-[2-(4-chloro-phenyl)-2,4,5,6-tetrahydro-cyclopentapyrazol-3-yl]-2-cyclohexyl-ethoxy}-3-fluoro-benzonitrile,
2-[2-(4-chloro-phenyl)-2,4,5,6-tetrahydro-cyclopentapyrazol-3-yl]-2,N-dicyclohexyl-acetamide,
2-(4-chloro-phenyl)-3-{1-cyclohexyl-2-[2-fluoro-4-(2H-tetrazol-5-yl)-phenoxy]-ethyl}-2,4,5,6-tetrahydro-cyclopentapyrazole,
4-{2-[2-(4-chloro-phenyl)-2,4,5,6-tetrahydro-cyclopentapyrazol-3-yl]-2-cyclohexyl-acetylamino}-3-fluoro-benzoic acid,
6-{2-[2-(4-chloro-phenyl)-2,4,5,6-tetrahydro-cyclopentapyrazol-3-yl]-2-cyclohexyl-ethoxy}-nicotinic acid,
4-{2-[2-(4-chloro-phenyl)-2,4,5,6-tetrahydro-cyclopentapyrazol-3-yl]-2-cyclohexyl-ethylsulfanyl}-benzoic acid,
2-(4-{2-[2-(4-chloro-phenyl)-2,4,5,6,7,8-hexahydro-cycloheptapyrazol-3-yl]-2-cyclohexyl-acetylamino}-3-fluoro-phenoxy)-2-methyl-propionic acid ethyl ester,
2-(4-{2-[2-(4-chloro-phenyl)-2,4,5,6,7,8-hexahydro-cycloheptapyrazol-3-yl]-2-cyclohexyl-acetylamino}-3-fluoro-phenoxy)-2-methyl-propionic acid,
2-[2-(4-chloro-phenyl)-2,4,5,6,7,8-hexahydro-cycloheptapyrazol-3-yl]-2,N-dicyclohexyl-acetamide,
4-{2-[2-(4-chloro-phenyl)-2,4,5,6,7,8-hexahydro-cycloheptapyrazol-3-yl]-2-cyclohexyl-acetylamino}-3-fluoro-benzoic acid methyl ester,
4-{2-[2-(4-chloro-phenyl)-2,4,5,6,7,8-hexahydro-cycloheptapyrazol-3-yl]-2-cyclohexyl-acetylamino}-3-fluoro-benzoic acid,
4-{2-[2-(4-chloro-phenyl)-2,4,5,6,7,8-hexahydro-cycloheptapyrazol-3-yl]-2-cyclohexyl-ethoxy}-3-fluoro-benzonitrile,
4-{2-[2-(4-chloro-phenyl)-2,4,5,6,7,8-hexahydro-cycloheptapyrazol-3-yl]-2-cyclohexyl-ethoxy}-3,5-dimethyl-benzoic acid,
2-(4-chloro-phenyl)-3-{1-cyclohexyl-2-[2-fluoro-4-(1H-tetrazol-5-yl)-phenoxy]-ethyl}-2,4,5,6,7,8-hexahydro-cycloheptapyrazole,
and pharmaceutically acceptable salts thereof.

In particular, the invention relates to compounds of formula I selected from the group consisting of
4-{2-[2-(4-chloro-phenyl)-2,4,5,6-tetrahydro-cyclopentapyrazol-3-yl]-2-cyclohexyl-ethoxy}-3,5-dimethyl-benzoic acid,
4-{2-[2-(4-chloro-phenyl)-2,4,5,6-tetrahydro-cyclopentapyrazol-3-yl]-2-cyclohexyl-ethoxy}-3-fluoro-benzonitrile,
2-(4-chloro-phenyl)-3-{1-cyclohexyl-2-[2-fluoro-4-(2H-tetrazol-5-yl)-phenoxy]-ethyl}-2,4,5,6-tetrahydro-cyclopentapyrazole,
4-{2-[2-(4-chloro-phenyl)-2,4,5,6-tetrahydro-cyclopentapyrazol-3-yl]-2-cyclohexyl-acetylamino}-3-fluoro-benzoic acid,
6-{2-[2-(4-chloro-phenyl)-2,4,5,6-tetrahydro-cyclopentapyrazol-3-yl]-2-cyclohexyl-ethoxy}-nicotinic acid,
4-{2-[2-(4-chloro-phenyl)-2,4,5,6,7,8-hexahydro-cycloheptapyrazol-3-yl]-2-cyclohexyl-acetylamino}-3-fluoro-benzoic acid,
2-(4-chloro-phenyl)-3-{1-cyclohexyl-2-[2-fluoro-4-(1H-tetrazol-5-yl)-phenoxy]-ethyl}-2,4,5,6,7,8-hexahydro-cycloheptapyrazole,
and pharmaceutically acceptable salts thereof.

Specifically, the invention relates to a compound of formula I which is
4-{2-[2-(4-chloro-phenyl)-2,4,5,6-tetrahydro-cyclopentapyrazol-3-yl]-2-cyclohexyl-ethoxy}-3,5-dimethyl-benzoic acid.

The invention also relates to a compound of formula I which is
2-(4-chloro-phenyl)-3-{1-cyclohexyl-2-[2-fluoro-4-(2H-tetrazol-5-yl)-phenoxy]-ethyl}-2,4,5,6-tetrahydro-cyclopentapyrazole.

The invention further relates to a process for the manufacture of compounds of formula I as defined above, which process comprises reacting a carboxylic acid of the formula II

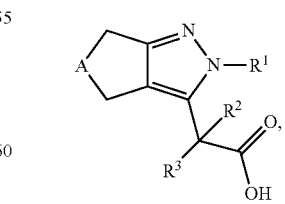

wherein A and $R^1$ to $R^3$ are as defined herein before, with an amine of the formula III $R^5$—$NH_2$       III, wherein R⁵ is a defined herein before, in the presence of a coupling reagent under basic conditions to obtain a compound of the formula Ia

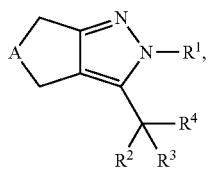

wherein R⁴ is —C(O)—NH—R⁵, and, if desired, converting the compound obtained into a pharmaceutically acceptable salt.

Appropriate coupling agents are for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP), with EDCI, TBTU or BOP being preferred. Under basic conditions means the presence of a base such as diisopropylethylamine, triethylamine, N-methylmorpholine, optionally in the presence of 4-dimethylamino-pyridine or HOBt (1-hydroxybenzo-triazole). The reaction is carried out in a suitable solvent such as for example dichloromethane, DMF, DMA or dioxane at temperatures between 0° C. and ambient temperature.

Alternatively, the invention provides a process for the manufacture of compounds of formula I as defined above, which process comprises reacting an alcohol of the formula IV

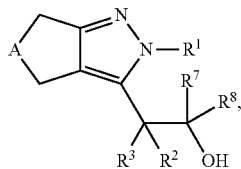

wherein A and R¹ to R³ and R⁷ and R⁸ are as defined herein before, with a compound of the formula V

X—R⁶    V, wherein R⁶ is as defined herein before and X denotes a halide, mesylate or tosylate moiety, or in case R⁶ corresponds to phenyl or phenyl substituted as defined herein efore, X denotes a hydroxy group,
to obtain a compound of formula Ib

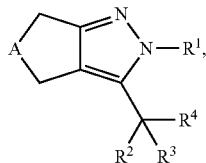

wherein R⁴ is —CR⁷R⁸—OR⁶, and, if desired, converting the compound obtained into a pharmaceutically acceptable salt.

Compounds of formula V, wherein X denotes a halide, mesylate or tosylate moiety, can be reacted with compounds of formula IV in the presence of a weak base like cesium or potassium carbonate in solvents like N,N-dimethylformamide, acetonitrile, acetone or methyl-ethyl ketone at a temperature ranging from room temperature to 140° C., preferably around 50° C., whereas compounds of formula V, wherein X denotes a hydroxy group can be reacted with compounds of formula IV in the presence of triphenylphosphine and di-tert-butyl-, diisopropyl- or diethyl-azodicarboxylate or in the presence of tributylphosphine and N,N,N',N'-tetramethyl azodicarboxamide, preferably in a solvent like toluene, dichloromethane or tetrahydrofuran at ambient temperature.

Alternatively, the invention relates to a process for the manufacture of compounds of formula I as defined above, which process comprises reacting an alcohol of the formula IV

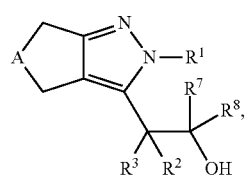

wherein A and R¹ to R³ and R⁷ and R⁸ are as defined herein before, with a lower alkyl-, lower fluoroalkyl- or phenylsulfonic acid chloride or -anhydride in the presence of a base to obtain an intermediate

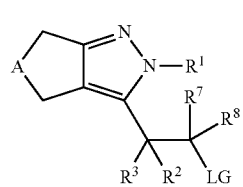

wherein LG signifies a —OSO₂-lower alkyl, —OSO₂-lower fluoroalkyl or —OSO₂-phenyl group, and reacting the intermediate in the presence of a base with an thiol

HS—R⁶    VII, wherein R⁶ is as defined herein before, to obtain a compound of formula Ic

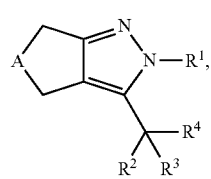

wherein R⁴ is —CR⁷R⁸—SR⁶, and, if desired, converting the compound obtained into a pharmaceutically acceptable salt, Alternatively, the invention provides a process for the manufacture of compounds of formula I as defined above, which process comprises reacting an alcohol of the formula VIII

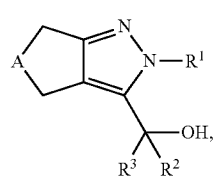

wherein A and R¹ to R³ are as defined herein before, with a compound of the formula IX

X—CR⁷R⁸—R⁶    IX, wherein R⁶ to R⁸ are as defined in claim 1 and X denotes a halide, mesylate or tosylate moiety, to obtain a compound of formula Id

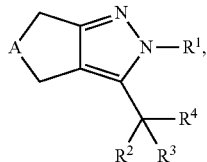

wherein R⁴ is —CR⁷R⁸—R⁶, and, if desired, converting the compound obtained into a pharmaceutically acceptable salt.

In more detail, the compounds of formula I, which are the subject of this invention, can be manufactured as outlined in schemes A, B, C, D, E, F, G, H, I and J, by the methods given in the examples or by analogous methods. Unless otherwise indicated, A, R¹, R², R²', R³, R³', R⁴, R⁴', R⁵, R⁵', R⁶, R⁷, R⁸ and n are as described above. The starting materials are either commercially available, described in the literature or can be prepared by methods well known in the art.

Scheme A

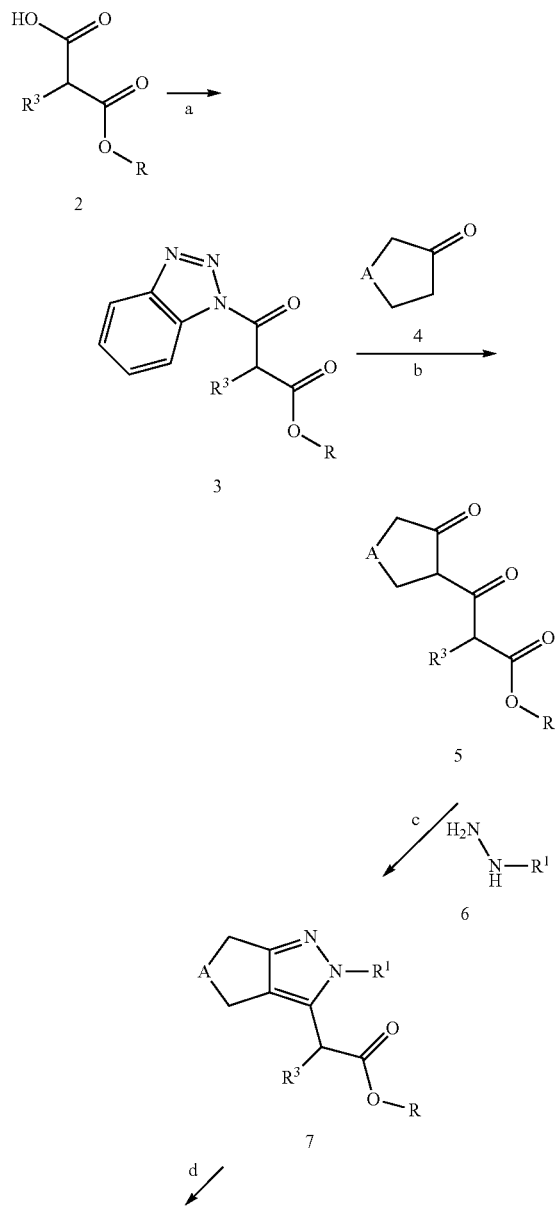

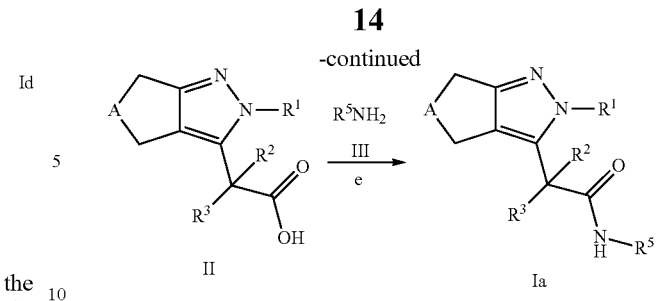

Alternatively, cyclopentyl- and cycloheptylpyrazoles of formula Ia can be prepared starting from 2-substituted malonic acid mono esters 2 (R e.g. corresponds to $C_{1-7}$-alkyl, scheme A). Malonic acid derivatives 2 are commercially available, described in the literature or can be synthesized by methods well known to a person skilled in the art. To facilitate the conversion of malonic acid derivatives 2 into bis-keto esters 5 the acid group of compounds 2 can e.g. be transformed into benzotriazol-1-yl amides 3 (step a). This transformation can e.g. be achieved via i) treatment of acids 2 with thionyl chloride, preferably under reflux conditions to form the corresponding acid chloride (alternative method: carboxylic acid 2, $CH_2Cl_2$, $(ClCO)_2$, DMF, rt); and ii) subsequent reaction with 1,2,3-benzotriazole in the presence of a base such as triethylamine or the like, preferably in a solvent like dichloromethane at temperatures between −20° C. and ambient temperature. Benzotriazoles 3 can than be converted into bis-keto esters 5 via reaction with a deprotonated ketone (derived from ketone 4), preferably in a solvent such as tetrahydrofuran or the like (step b). Deprotonation can be achieved using a base such as lithium diisopropylamide in a solvent such as tetrahydrofuran or the like at temperatures between −78° C. and ambient temperature. Ketones 4 are commercially available, described in the literature or can be synthesized by methods well known to a person skilled in the art. Condensation of bis-ketones 5 with (hetero)aromatic hydrazines 6 or a salt e.g. the hydrochloride salt of (hetero) aromatic hydrazines 6 gives cyclopentyl- or cycloheptylpyrazole esters 7 (step c). Preferably, such condensations are carried out in a solvent such as ethanol and the like, at the reflux temperature of the solvent employed. (Hetero)aromatic hydrazines 6 or the corresponding (hetero)aromatic hydrazine salts are commercially available, described in the literature or can be synthesized by methods well known to a person skilled in the art. Esters 7 can be saponified to form acids of formula II, using e.g. aqueous LiOH, NaOH or KOH in tetrahydrofuran/ethanol or another suitable solvent at temperatures between 0° C. and the reflux temperature of the solvent employed (step d). Acids of formula II—after suitable activation—can be coupled with amines of formula III to amides of formula Ia using standard peptide coupling procedures described in the literature (step e). Activation of carboxylic acids of formula II can be performed using methods well known to a person skilled in the art. (e.g. carboxylic acid chlorides: 1. carboxylic acid, $CH_2Cl_2$, $(ClCO)_2$, DMF, rt; or 2. carboxylic acid, thionyl chloride, reflux). Alternatively, carboxylic acids of formula II can be in situ activated and transformed into the final products of formula Ia using coupling reagents such as e.g. N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP).

Preferably, EDCI, TBTU or BOP are used. The reaction is carried out in the presence of a base such as diisopropylethylamine, triethylamine, N-methylmorpholine, optionally in the presence of 4-dimethylamino-pyridine or HOBt (1-hydroxybenzo-triazole), in solvents such as dichloromethane, DMF, DMA or dioxane at temperatures between 0° C. and ambient temperature. Amines of formula III are commercially available, described in the literature or can be prepared by methods well known to a person skilled in the art.

Amides of formula Ia can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane in the case of e.g. tert-butyl esters. Optionally, 4,5,6,7-tetrahydroindazoles of formula Ia can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae 2, 4, 6 or III, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If one or more compounds of the formulae 2 to 7, II or III contain chiral centers, cyclopentyl- or cycloheptylpyrazoles of formula Ia can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R) or (S)-1-phenyl-ethylamine, (R) or (S)-1-naphthalen-1-yl-ethylamine, brucine, quinine or quinidine) or by separation of the antipodes by specific chromatographic methods using either a chiral adsorbens or a chiral eluent.

Scheme B

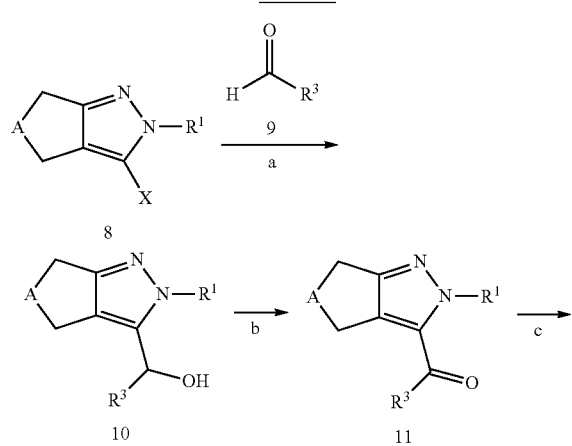

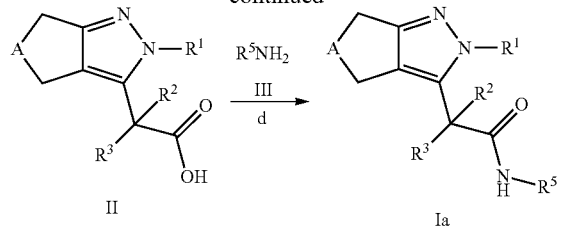

Cyclopentyl- and cycloheptylpyrazoles 8, wherein X corresponds to H, Cl, Br or I, are described in the literature, can be prepared by methods well known to a person skilled in the art or by methods described in scheme E. Cyclopentyl- and cycloheptylpyrazoles 8 can be converted into alcohols 10 e.g. via treatment with a strong base such as n-buthyllithium in a solvent like tetrahydrofuran preferably at a temperature between −78° C. and 0° C. and subsequent addition of an aldehyde of formula 9 (step a). Aldehydes 9 are commercially available, described in the literature or can be prepared by methods well known to a person skilled in the art.

Alcohols 10 can be oxidized to ketones 11 applying standard literature procedures, e.g. 2-iodoxybenzoic acid in a mixture of tetrahydrofuran and dimethylsulfoxide, preferably at temperatures between 0° C. and ambient temperature (step b).

Ketones 11 can be transformed into acids of formula II using e.g. the following reaction sequence: i) reaction of ketones 11 with trimethylsilyl cyanide using catalytic amounts of zinc (II) iodide to the corresponding trimethylsilanyloxy-acetonitriles, preferably at temperatures between ambient temperature and 50° C.; ii) subsequent one pot reduction with tin (II) chloride and hydrolysis to acids of formula II in a solvent mixture consisting of concentrated aqueous hydrochloric acid and acetic acid, preferably at the reflux temperature of the solvent mixture employed (step c).

Acids of formula II—after suitable activation—can be coupled with amines of formula III to amides of formula Ia (compounds of formula I, wherein $R^4$ corresponds to —C(O)—NH—$R^5$) using standard peptide coupling procedures described in the literature (step d). Activation of carboxylic acids of formula II can be performed using methods well known to a person skilled in the art. For example, carboxylic acids of formula II can be transformed into carboxylic acid chlorides by solving the acid in dichloromethane and reacting it with $(ClCO)_2$ in DMF at room temperature or by reacting it with neat thionyl chloride at reflux temperature. Alternatively, carboxylic acids of formula II can be in situ activated and transformed into the final products of formula Ia using coupling reagents such as e.g. N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP). Preferably, EDCI, TBTU or BOP are used. The reaction is carried out in the presence of a base such as diisopropylethylamine, triethylamine, N-methylmorpholine, optionally in the presence of 4-dimethylamino-pyridine or HOBt (1-hydroxybenzo-triazole), in solvents such as dichloromethane, DMF, DMA or dioxane at temperatures between 0° C. and ambient temperature.

Amines of formula III are commercially available, described in the literature or can be prepared by methods well known to a person skilled in the art. To introduce residues $R^2 \ne$hydrogen, carboxylic acids of formula II can e.g. i) be converted into the corresponding carboxylic acid esters applying standard literature methods (e.g. heating acid of formula II with a primary or secondary alcohol in the presence of a catalyst such as sulfuric acid, preferably under reflux conditions); ii) treatment of the obtained ester with a base and an alkylating reagent using methods known to a person skilled in the art (e.g. lithium diisopropylamide as a base and an alkyl halide as alkylating reagent in a solvent such as tetrahydrofuran at temperatures between −78° C. and the reflux temperature of the solvent employed). Optionally, such alkylations can be carried out in an enantioselective or diastereoselective fashion using either alcohols which contain a chiral center in the esterification step and/or a chiral catalyst in the alkylation step; iii) saponification of the ester to form substituted carboxylic acids of formula II (e.g. using aqueous LiOH, NaOH or KOH in tetrahyrofuran/ethanol or another suitable solvent). Acids of formula II with $R^2$=F can e.g. be synthesized via direct fluorination of the corresponding silyl ketene acetal using 1-chloromethyl-4-fluoro-1,4-diazoniabicyclo[2.2.2]octane bis-(tetrafluoroborate) following a procedure described in F. Zhang, J. Z. Song, Tetrahedron Lett. 2006, 47, 7641-7644.

Amides of formula Ia can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane in the case of e.g. tert-butyl esters. Optionally, cyclopentyl- or cycloheptylpyrazoles of formula Ia can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae 8, 9 or III, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2nd Ed., 1991, Wiley N.Y.) can be introduced before the critical step applying methods well known in the art. Such protecting groups can be removed at a later stage of the synthesis using standard methods described in the literature.

If one or more compounds of formulae 8 to 11, II or III contain chiral centers, cyclopentyl- or cycloheptylpyrazoles of formula Ia can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R) or (S)-1-phenyl-ethylamine, (R) or (S)-1-naphthalen-1-yl-ethylamine, brucine, quinine or quinidine) or by separation of the antipodes by specific chromatographic methods using either a chiral adsorbens or a chiral eluent.

Scheme C

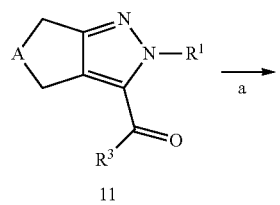

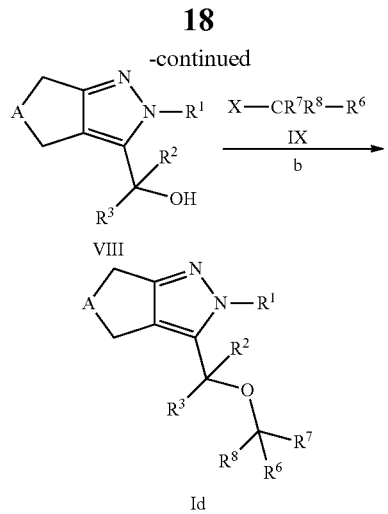

Cyclopentyl- and cycloheptylpyrazole ethers of formula Ib (compounds of formula I wherein $R^4$ is —O—$CR^7R^8$—$R^6$) can be prepared starting from ketones 11 (scheme B). Ketones 11 can be converted into alcohols of formula IV (for $R^2$=H equal to compounds 10 in scheme B) applying standard methods described in the literature (step a). Treatment of ketones 11 with an alkyllithium reagent $R^2$Li in solvents like ether or tetrahydrofuran gives tertiary alcohols of formula VIII (step a); treatment of ketones 11 with lithium aluminium hydride in solvents like tetrahydrofuran or diethyl ether or with sodium borohydride in solvents like ethanol or methanol, preferably at temperatures between −15° C. and 40° C., gives alcohols of formula VIII with $R^2$=H (step a). The alcohol compounds of formula VIII which contain a chiral center can optionally be separated into optically pure antipodes by methods well known in the art, e.g. chromatography on a chiral HPLC column, or by derivatization with an optically pure acid to form esters, which can be separated by conventional HPLC chromatography and can then be converted back to the enantiomerically pure alcohols of formula VIII. Alternatively, the reduction of ketones 11 to the corresponding secondary alcohols of formula IV can also be carried out in an enantioselective fashion leading to the (R)- or (S)-alcohols of formula IV, e.g. by treatment with borane-dimethylsulfide complex and (S)- or (R)-2-methyl-CBS-oxazaborolidine ((S)- or (R)-1-methyl,3,3-diphenyl-tetrahydro-pyrrolo(1,2-c)(1,3,2)oxazaborole) as chiral catalyst in tetrahydrofuran, preferably at temperatures between −78° C. and ambient temperature, according to Corey et al. (E. J. Corey, R. K. Bakshi, S. Shibata, J. Am. Chem. Soc. 1987, 109, 5551-5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, Tetrahedron: Asymmetry 1994, 5, 1061-1074).

Alcohols of formula VIII are condensed with compounds of formula IX according to well known procedures. If X represents a halide, mesylate or tosylate moiety, alcohols of formula VIII can be reacted with compounds of formula IX in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds of formula Id (step b).

Ethers of formula Id can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane e.g. in the case of tert-butyl esters. Optionally, cyclopentyl- or cycloheptylpyrazoles of formula Id can also contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae 11 or IX, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae 11, VIII or IX contain chiral centers, cyclopentyl- or cycloheptylpyrazoles of formula Ib can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

Scheme D

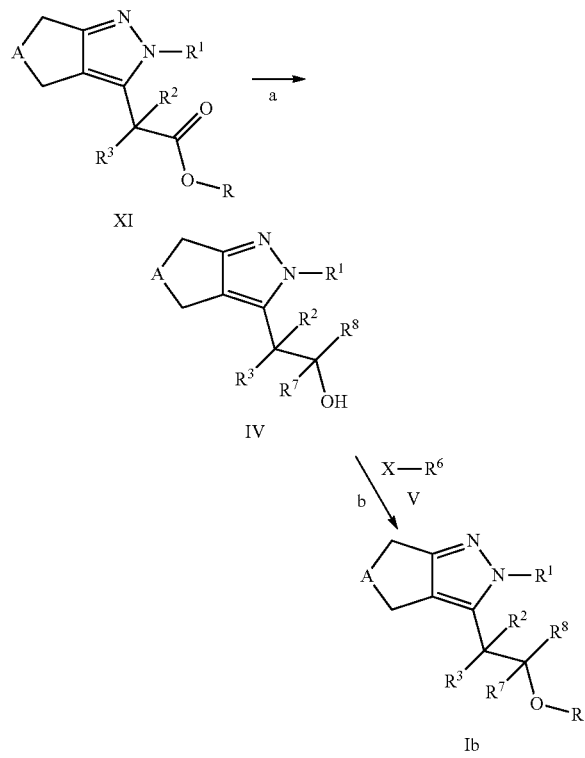

Cyclopentyl- and cycloheptylpyrazole ethers of formula Ib (compounds of formula I wherein $R^4$ is —$CR^7R^8$—$OR^6$) can be prepared starting from acids of formula XI (R=H, compounds of formula II in schemes A and B) or esters of formula XI (R e.g. corresponds to $C_{1-7}$-alkyl, compounds 7 in scheme A). Acids of formula XI (R=H) can be converted into esters (R e.g. equal to $C_{1-7}$-alkyl) applying standard literature procedures, e.g. heating acid of formula XI (R=H) with a primary or secondary alcohol in the presence of a catalyst such as sulfuric acid, preferably under reflux conditions. Acids of formula XI (R=H) can be further transformed into primary alcohols of formula IV ($R^7$=H, $R^8$=H), e.g. by using diborane in tetrahydrofuran (step a). Esters of formula XI (R e.g. equal to $C_{1-7}$-alkyl) can be reduced, e.g. with lithium aluminum hydride in solvents like ether or tetrahydrofuran, to alcohols of formula IV with $R^7$=$R^8$=H (step a). Alternatively, substituents $R^7$ and/or $R^8$ different from hydrogen can be introduced to acids of formula XI (R=H) by i) treatment with $R^7$Li optionally in the presence of a Cu (I) salt in ether or tetrahydrofuran to yield the alkyl ketones —$COR^7$; ii) subsequent reaction with $R^8$Li or lithium aluminium hydride in ether or tetrahydrofuran (step a). The alcohol compounds of formula IV which contain a chiral center can optionally be separated into optically pure antipodes by methods well known in the art, e.g. chromatography on a chiral HPLC column, or by derivatization with an optically pure acid to form esters, which can be separated by conventional HPLC chromatography and can then be converted back to the enantiomerically pure alcohols of formula IV. The reduction of alkyl ketones —$COR^7$ to the corresponding secondary alcohols of formula IV of scheme D can also be carried out in an enantioselective fashion leading to the (R)- or (S)-alcohols of formula IV, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheyl-borane (DIP-C1), according to Brown et al. (P. V. Ramachandran, B. Gong, A. V. Teodorovic, H. C. Brown, *Tetrahedron: Asymmetry* 1994, 5, 1061-1074).

Alcohols of formula IV are condensed with compounds of formula V according to well known procedures: if X represents a hydroxy group and $R^6$ is an aryl system e.g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature (step b). Alternatively, if X represents a halide, mesylate or tosylate moiety, alcohols of formula IV can be reacted with compounds V ($R^6$ not equal to an aryl system) in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds Ic (step b).

Ethers of formula Ib can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane e.g. in the case of tert-butyl esters. Optionally, cyclopentyl- or cycloheptylpyrazoles of formula Ic can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae V or XI, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae V, IV and XI contain chiral centers, cyclopentyl- or cycloheptylpyrazoles of formula Ic can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

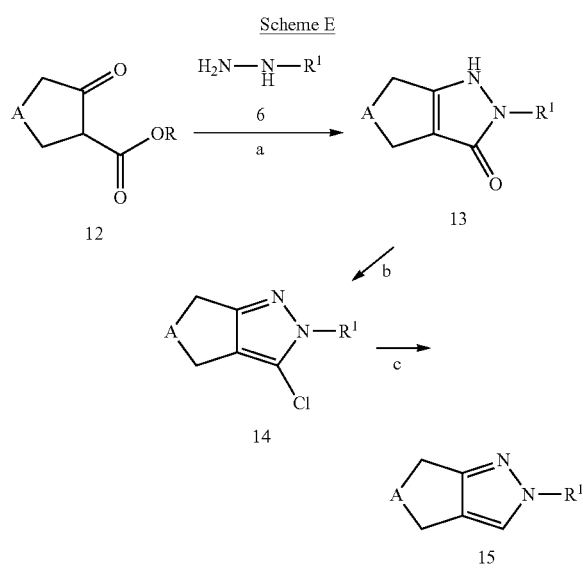

Scheme E

2-Substituted cyclopentyl- and cycloheptylpyrazoles 14 and 15 (corresponding to compounds 8 in scheme B) can be prepared starting from cyclopentanone or cycloheptanone-2-carboxylic acid esters 12 (R is e.g. $C_{1-7}$-alkyl) as described in scheme E. Cyclopentanone or cycloheptanone-2-carboxylic acid esters 12 are commercially available, described in the literature or can be synthesized by methods well known to a person skilled in the art. Condensation of keto esters 12 with (hetero)aromatic hydrazines 6 or a salt e.g. the hydrochloride salt of (hetero)aromatic hydrazines 6 gives 2-substituted pyrazole-3-ones 13 (step a). Preferably, such condensations are carried out in a solvent such as toluene and the like, at the reflux temperature of the solvent employed. (Hetero)aromatic hydrazines 6 or the corresponding (hetero)aromatic hydrazine salts are commercially available, described in the literature or can be synthesized by methods well known to a person skilled in the art. Pyrazole-3-ones 13 can be converted to 2-substituted 3-chloro-pyrazoles 14 e.g. by treatment with phosphorus oxychloride in the presence of catalytic amounts of N,N-dimethyl-anilin, preferably under reflux conditions (step b). Transformation of 3-chloro-pyrazoles 14 into 2-substituted pyrazoles 15 can e.g. be achieved using hydrogen gas in the presence of a transition metal catalyst like palladium on charcoal (step c).

If one of the starting materials, compounds of formulae 12 or 6, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds 12, 6 or 13 contain chiral centers, 2-substituted pyrazoles 14 and 15 can be obtained as mixtures of diastereomers or enantiomers, which can be separated by methods well known in the art, e.g. (chiral) HPLC or crystallization. Racemic compounds can e.g. be separated into their antipodes by specific chromatographic methods using either a chiral adsorbens or a chiral eluent.

Compounds of general structure Ic to Ig can be prepared according to Scheme F from intermediates of type 16. Intermediates 16 can be prepared in the case LG signifies a —$OSO_2$alkyl, —$OSO_2$-fluoroalkyl or —$OSO_2$aryl group by treatment of alcohol IV (Scheme D) with, e.g. an alkyl-, fluoroalkyl- or arylsulfonic acid chloride or -anhydride in a suitable solvent such as, e.g. dichloromethane and using an appropriate base such as, e.g. Hünig's base or pyridine (step a). Reaction of intermediates 16 with, e.g. optionally substituted alkyl- or aryl-thiols 17 (VII) with a suitable base such as, e.g. sodium hydride in an appropriate solvent such as, e.g. N,N-dimethylformamide furnishes compounds Ic (step b). Compounds Ic can be converted into compounds Ie through oxidation of the sulfur atom with an oxidizing agent such as, e.g. 3-chloroperoxybenzoic acid in a suitable solvent such as, e.g. dichloromethane (step c). In case compounds Ic and Ie carry a carboxylic ester group these can be cleaved by methods known to those skilled in the art and as described for example in "Protective Groups in Organic Chemistry" by T. W. Greene and P. G. M. Wutts, 2nd Ed., 1991, Wiley N.Y.) to yield the corresponding carboxylic acids. For example, a benzyl ester can be cleaved by catalytic hydrogenation using an appropriate catalyst such as, e.g. palladium on charcoal in a suitable solvent such as, e.g. methanol, ethanol, ethyl acetate, tetrahydrofuran or mixtures of said solvents. An alkyl ester such as, e.g. a methyl or ethyl ester can be cleaved under basic conditions (e.g. with lithium or sodium hydroxide in polar solvents such as, e.g. methanol, water or tetrahydrofuran or mixtures of said solvents). A tert-butyl ester can be cleaved for example under acidic conditions (e.g. using trifluoroacetic acid, optionally in an appropriate solvent such as, e.g. dichloromethane and optionally using a nucleophilic scavenger such as, e.g. 1,3-dimethoxybenzene or thioanisole, or using concentrated hydrochloric acid in tetrahydrofuran or formic acid in an appropriate solvent such as an alcohol like, e.g. isopropanol). An allyl ester can be cleaved for example in a transition metal-catalyzed reaction using, e.g. tetrakis (triphenylphenyl)palladium as catalyst together with pyrrolidine or morpholine in tetrahydrofuran as solvent.

Scheme F

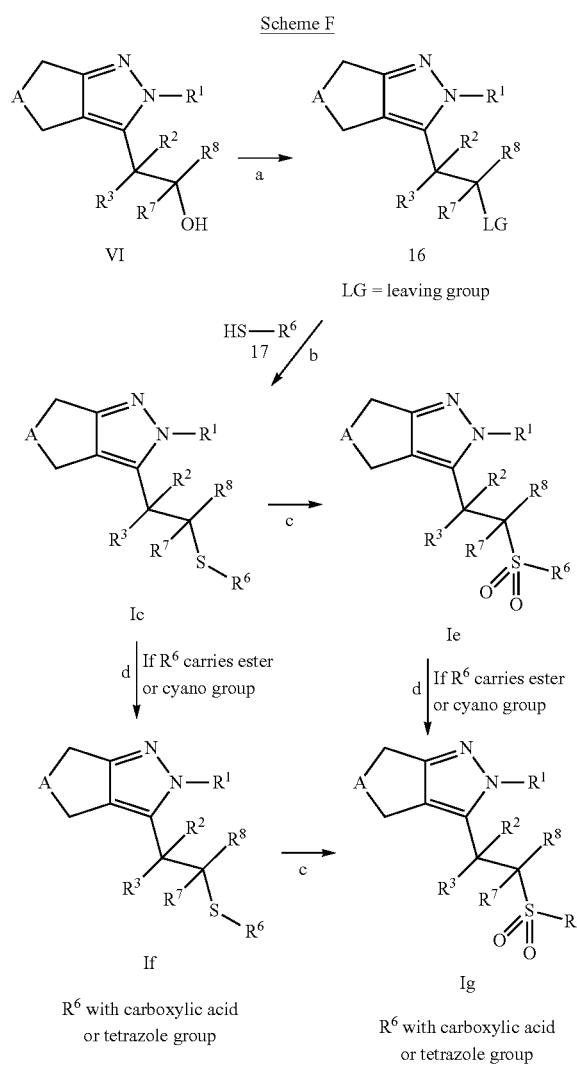

R[6] with carboxylic acid or tetrazole group

R[6] with carboxylic acid or tetrazole group

Optionally, compounds Ic and Ie can also contain cyano groups which can be either hydrolyzed to the carboxylic acid under basic (e.g. with aqueous sodium or lithium hydroxide) or acidic conditions (e.g. hydrochloric or sulphuric acid) or can be converted to the corresponding tetrazoles using standard procedures such as, e.g. by treatment with sodium azide in the presence of a Lewis acid or ammonium chloride in water or organic solvents like dichloromethane or N,N-dimethylformamide at temperatures between 0° C. and the boiling point of the solvent to furnish compounds If and Ig (step d).

Alternatively, compounds of the formula Ig can be synthesized by oxidation of compounds If (step c) applying the methods described above.

If one of the starting materials, compounds of formulae IV or 17 (VII), contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds of formulae IV and 17 (VII) contain chiral centers, cyclopentyl- or cycloheptylpyrazoles of formula Ic, Ie, If and Ig can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

Scheme G

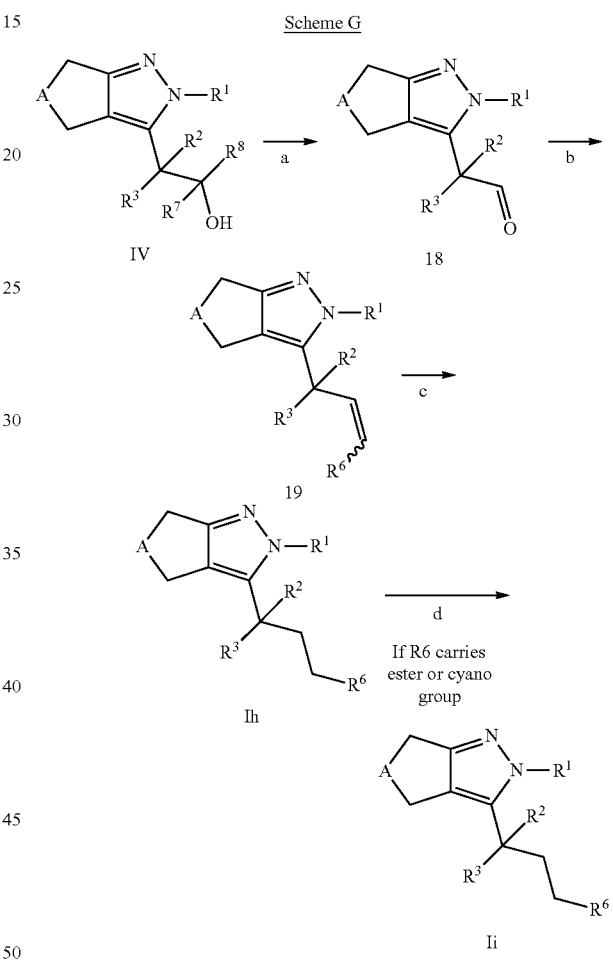

If R6 carries ester or cyano group

Compounds of general structure Ih and Ii in which R[7]=R[8]=H can be prepared according to Scheme G. Aldehydes 18 can be synthesized by oxidation of intermediates IV (step a). Reactions of this type are known to those skilled in the art and are widely used and described in the literature (e.g. "March's Advanced Organic Chemistry" by M. B. Smith and J. March, 7$^{th}$ ed., 2007, Wiley & Sons N.Y.). For example, intermediate IV can be oxidized with, e.g. 1,1,1-triacetoxy-1,1-dihydro-1,2-benziodoxol-3(1H)-one in an appropriate solvent such as, e.g. dichloromethane or chloroform. Intermediates 19 are accessible by, e.g. Wittig reaction which is well known to those skilled in the art. For example, intermediate 18 is reacted with an optionally substituted benzyl-triphenyl-phosphonium chloride or bromide (either commercially available or synthesized by methods known in the art) in the presence of a suitable base and a solvent such as, e.g.

potassium tert-butylate, butyllithium or sodium hydride in, e.g. tetrahydrofuran (step b). Depending on the reaction conditions intermediates 19 can exist as cis, trans or mixture of cis/trans isomers. Intermediates 19 can be transformed into compounds Ih by, e.g. catalytic hydrogenation using a transition metal catalyst such as, e.g. palladium or platinum on charcoal in an appropriate solvent such as, e.g. ethyl acetate, methanol or ethanol or mixtures of said solvents (step c).

Optionally compounds Ih can contain ester or cyano groups that can be converted into the corresponding carboxylic acid and tetrazole groups, respectively, applying the conditions described before, to furnish compounds Ii (step d).

If one of the starting materials, compounds of formulae IV or the substituted benzyl-triphenyl-phosphonium chloride or bromide, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae IV and the substituted benzyl-triphenyl-phosphonium chlorides or bromides contain chiral centers, cyclopentyl- or cycloheptylpyrazoles of formula Ih and Ii can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

Scheme H

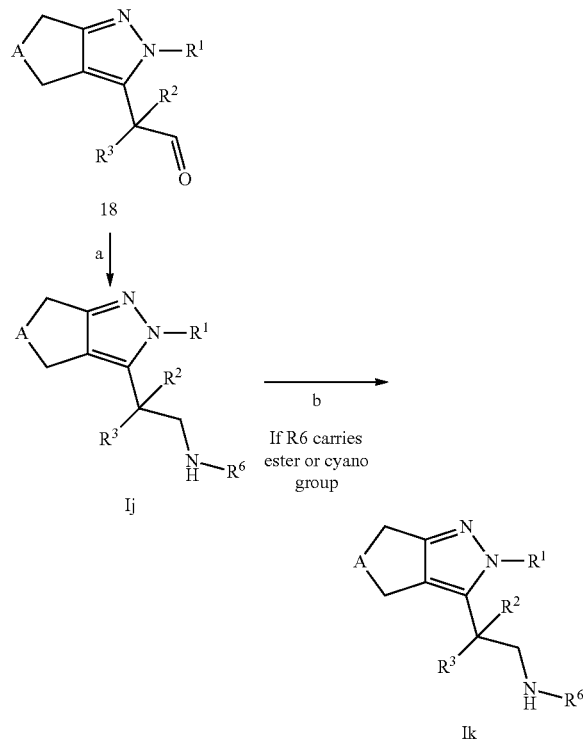

Compounds of the general formula Ij and Ik in which $R^7=R^8=H$ can be prepared as described in Scheme H. Intermediates 18 (prepared as described in Scheme G) are reacted with an alkyl- or optionally substituted arylamine in the presence of a reducing agent such as, e.g. cyanoborohydride, sodium triacetoxyborohydride or di-n-butyltin dichloride with triphenysilane in an appropriate solvent such as, e.g. tetrahydrofuran to furnish compounds Ij (step a). In those cases where compounds Ij contain ester or cyano groups, these can be converted into the corresponding carboxylic acid and tetrazole groups (step b), respectively, applying the conditions described above.

If one of the starting materials, compounds of formulae 18 or the alkyl- or optionally substituted arylamine, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae 18 and the alkyl- or optionally substituted arylamine contain chiral centers, cyclopentyl- or cycloheptylpyrazoles of formula Ij and Ik can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

Alternatively, compounds Il and Im can be prepared according to Scheme I. Carboxylic acids VIII (R=H, see Scheme D) can be transformed into intermediates 20 by, e.g. treating the acid group in VIII with an activating agent such as, e.g. N-hydroxybenzotriazole monohydrate, optionally together with 1-ethyl-3-(3-dimethyllaminopropyl)carbodiimide hydrochloride, in the presence of a base such as, e.g. ethyl diisopropylamine in a suitable solvent such as, e.g. N,N-dimethylformamide and an ammonia source such as, e.g. ammonium chloride (step a). The amide group in intermediates 20 can be converted to the corresponding amine by, e.g. treatment with a reducing agent such as, e.g. lithium aluminium hydride in a suitable solvent such as, e.g. tetrahydrofuran to give intermediate 21 with $R^7=R^8=H$ (step b). Intermediates 21 with $R^7$ and $R^8$ as defined above can be alternatively obtained from intermediates 16 (prepared as described in Scheme F) by converting them to the azide (intermediate 22, step e) by, e.g. reaction with sodium azide in a suitable solvent such as, e.g. N,N-dimethylformamide and reduction of the azide to the amine (step f) by, e.g. catalytic hydrogenation applying the same methods as described above. Intermediates 21 can be transformed into compounds of formula Il though alkylation or reductive amination according to the methods described before (step c). In case compounds Il contain ester or cyano groups they can be converted to the corresponding carboxylic acid and tetrazole groups, respectively, applying the conditions described before, to furnish compounds Im (step d) wherein $R^6$ contains a carboxylic acid or tetrazole group. If one of the starting materials, compounds of formulae VIII, 16 or the alkylating reagents, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae VIII, 16 or the alkylating reagents contain chiral centers, cyclopentyl- or cycloheptylpyrazoles of formula Il and Im can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenylethylamine, (R)- or (S)-1-naphthalen-1-yl-ethylamine, brucine, quinine or quinidine) or by separation of the antipodes by specific chromatographic methods using either a chiral adsorbens or a chiral eluent.

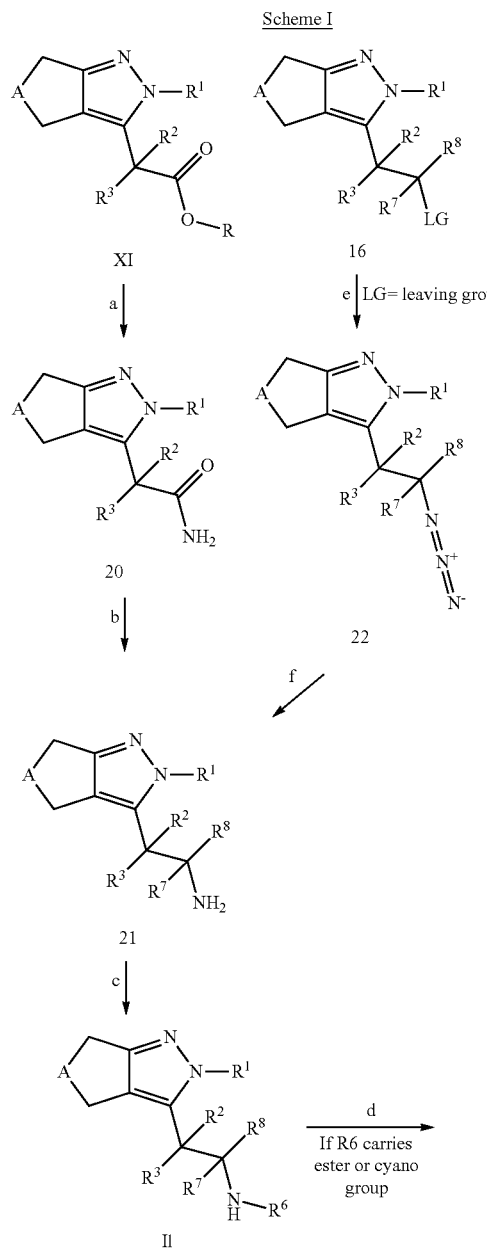

Compounds In and Ir can also be prepared according to Scheme J if substituents $R^1$ to $R^8$ are stable under the reducing conditions applied in step b. Amide coupling of intermediates XI (R=H) with optionally substituted amines $R^6NH_2$ (either commercially available or accessible by methods described in references or by methods known in the art) gives compounds 23 (step a). Amide couplings of this type are widely described in the literature (e.g. Comprehensive Organic Transformations: A Guide to Functional Group Preparations, 2nd Edition, Richard C. Larock, John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. N,N-dimethylformamide (DMF) or dioxane, optionally in the presence of a base (e.g. triethylamine, diisopropylethylamine or 4-(dimethylamino)pyridine). Alternatively, intermediates 28 can be obtained by converting intermediates XI (R=H) into the corresponding acid chlorides by treatment with, e.g. thionyl chloride, optionally in a solvent such as, e.g. dichloromethane and reaction of the acid chloride with optionally substituted cycloalkyl/(hetero)aryl amines in an appropriate solvent such as, e.g. dichloromethane and a base such as, e.g. triethylamine, pyridine diisopropylethylamine or 4-(dimethylamino)pyridine. Conversion of intermediates 23 into compounds In with $R^7=R^8=H$ (step b) can be accomplished for example by treating intermediates 23 with a suitable reducing agent such as, e.g. lithium aluminium hydride, di-isobutylaluminium hydride or borane dimethyl sulfide or tetrahydrofuran complex in a suitable solvent such as, e.g. diethyl ether, tert-butyl methyl ether or tetrahydrofuran at temperatures between 0° C. and the boiling point of the solvent. Conversion of compounds In into Io wherein $R^6$ signifies a carboxylic acid of tetrazole group (step d) can be accomplished according to the methods described above.

If one of the starting materials, compounds of formulae XI or amines $R^6NH_2$, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae XI or amines $R^6NH_2$, contain chiral centers, cyclopentyl- or cycloheptylpyrazoles of formula In and Io can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

If desired or required functional groups present in compound of formula I (such as —$CO_2$alkyl, amino groups, cyano groups and others) may be derivatized to other functional groups using typical standard procedures known to those skilled in the art (e.g. reduction of —$CO_2$alkyl to —$CH_2OH$ with $LiAlH_4$, hydrolysis of —$CO_2$alkyl to —$CO_2H$ and subsequent optional conversion to an amide, acylation of amino groups).

As described above, the novel compounds of the present invention have been found to bind to and selectively activate FXR. They can therefore be used in the treatment or prophylaxis of diseases and conditions that are affected by FXR modulators. Particularly, the FXR modulators are FXR agonists.

"Diseases which are affected by FXR modulators" include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

In particular, diseases (and conditions) which are affected by FXR modulators are prevention or treatment of high LDL cholesterol levels, high triglycerides, dyslipidemia, cholesterol gallstone disease, cancer, non-insulin dependent diabetes mellitus and metabolic syndrome. Specifically, diseases which are affected by FXR modulators are high LDL cholesterol, high triglyceride levels and dyslipidemia.

The invention therefore also relates to pharmaceutical compositions comprising a compound as defined above and a pharmaceutically acceptable carrier and/or adjuvant.

The invention likewise embraces compounds as described above for use as therapeutically active substances, especially for use in the treatment or prophylaxis of diseases which are affected by FXR modulators, particularly as therapeutically active substances for the treatment or prophylaxis of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

In another embodiment, the invention relates to a method for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease, which method comprises administering a compound as defined above to a human being or animal.

The invention also embraces the use of compounds as defined above for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

The invention also relates to the use of compounds as described above for the preparation of medicaments for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease. In particular, the invention provides for the use of compounds of formula I for the preparation of medicaments for the therapeutic or prophylactic treatment of high LDL cholesterol, high triglyceride levels and dyslipidemia, more specifically for dyslipidemia. Such medicaments comprise a compound as described above.

Also contemplated herein is a combination therapy using one or more compounds of formula I or compositions provided herein, or a pharmaceutically acceptable derivative thereof, in combination with one or more compounds selected from the group consisting of the following: cholesterol biosynthesis inhibitors (HMG CoA reductase inhibitors, e.g. lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g. thiazolidinediones e.g. rosiglitazone, troglitazone, and pioglitazone); PPAR alpha agonists (e.g. clofibrate, fenofibrate and gemfibronzil); PPAR dual alpha/gamma agonists (e.g. muraglitazar, aleglitazar, peliglitazar); bile acid sequestrants (e.g. anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-Coenzyme A:cholesterol O-acyl transferase (ACAT) inhibitors (e.g. avasimibe); selective estrogen receptor modulators (e.g. raloxifene or tamoxifen); LXR alpha or beta agonists, antagonists or partial agonists (e.g. 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g. metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g. pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g. sitagliptin phosphate, saxagliptin, vildagliptin, alogliptin or denagliptin), incretins (e.g. glucagon-like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buproprion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1 a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-$HT_{2C}$ (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g. orlistat); cyclooxygenase-2 (COX-2) inhibitors (e.g. rofecoxib and celecoxib); thrombin inhibitors (e.g. heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B 12; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; agents other than LXR ligands that enhance ATP-Binding Cassette Transporter-A1 gene expression; and bisphosphonate compounds (e.g. alendronate sodium).

The following tests were carried out in order to determine the activity of the compounds of formula I. Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21(pLysS) cells by standard methods (Current Protocols in Molecular Biology, Wiley Press, ed. Ausubel et al).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$. For each reaction well in a 96-well plate, 40 nM of GST-FXR LBD fusion protein was bound to 10 µg glutathione ytrium silicate SPA beads (Pharmacia Amersham) in a final volume of 50 µl by shaking A radioligand (eg. 40 nM) of 2,N-dicyclohexyl-2-[2-(2,4 dimethoxy-phenyl)-benzoimidazol-1-yl]-acetamide)

was added, and the reaction incubated at RT for 30 minutes in the presence of test compounds followed by scintillation proximity counting. All binding assays were performed in 96-well plates and the amount of bound ligand was measured on a Packard TopCount using OptiPlates (Packard). Dose response curves were performed within a range of concentration from $6\times10^{-9}$ M to $2.5\times10^{-5}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula I have an activity in at least one of the above assays ($EC_{50}$ or $IC_{50}$), preferably in the range of 0.5 nM to 10 μM, more preferably 0.5 nM to 100 nM. For example, compounds of formula I of the present invention showed the following $IC_{50}$ values in the binding assay described above:

| Example | $IC_{50}$ [μM] |
| --- | --- |
| 1 | 28.7 |
| 2 | 0.017 |
| 3 | 1.3 |
| 4 | 3.3 |
| 5 | 0.092 |
| 6 | 0.603 |
| 7 | 0.052 |
| 8 | 1.1 |
| 9 | 21.4 |
| 10 | 1.3 |
| 11 | 2.4 |
| 12 | 7.0 |
| 13 | 1.7 |
| 14 | 21.3 |
| 15 | 0.53 |
| 16 | 0.155 |

The compounds of formula I and their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. IN particular, the compounds of formula I can be used for oral administration.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations $CH_2Cl_2$=dichloromethane, d=day, DCM=dichloromethane, DIPEA=N,N-diisopropylethylamine, DMAP=4-(dimethylamino)-pyridine, DMF=N,N-dimethylformamide, DMSO=dimethyl sulfoxide, ee=enantiomeric excess, $Et_3N$=triethylamine, EtOAc=ethyl acetate, h=hour, HATU=2-(1H-7-azabenzotriazol-1-yl)-1,1,3,3-tetramethyl uronium hexafluorophosphate, HCl=hydrochloric acid, HPLC=high performance liquid chromatography, iPrOAc=isoproyl acetate, LDA=lithium diisopropylamide, LiHMDS=lithium hexamethyldisilazide, MeOH=methanol, min=minutes, NaHCO₃=sodium bicarbonate, NaOH=sodium hydroxide, Na₂SO₄=sodium sulfate, quant.=quantitative, rt=room temperature, TBME=tert-butylmethyl ether, THF=tetrahydrofuran, TLC=thin layer chromatography.

Example 1

4-{2-[2-(4-Chloro-phenyl)-2,4,5,6-tetrahydro-cyclopentapyrazol-3-yl]-2-cyclohexyl-ethoxy}-3,5-dimethyl-benzoic acid methyl ester

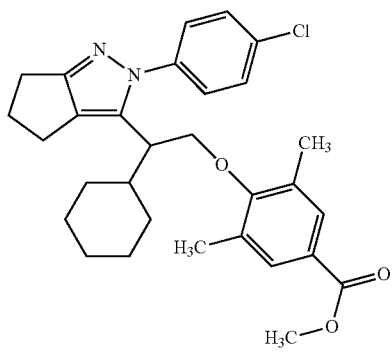

1.1 3-Benzotriazol-1-yl-2-cyclohexyl-3-oxo-propionic acid ethyl ester

A solution of 2-cyclohexyl-malonic acid monoethyl ester (2.9 g, 14 mmol; CAS Reg. No. 147596-63-2) in thionyl chloride (29 ml) was heated under reflux conditions for 2 h. The solvent was removed under reduced pressure to give chlorocarbonyl-cyclohexyl-acetic acid ethyl ester. 1,2,3-Benzotriazole (1.47 g, 12 mmol) was dissolved at ambient temperature under an argon atmosphere in CH₂Cl₂ (45 ml). Et₃N (1.86 ml, 13 mmol) and a solution of chlorocarbonyl-cyclohexyl-acetic acid ethyl ester in CH₂Cl₂ (4 ml) was added. The reaction mixture was stirred at ambient temperature for 14 h, quenched with ice cold aqueous 2 N HCl and extracted two times with iPrOAc. The combined extracts were washed with ice water/1 N aqueous HCl solution, ice water/brine 1/1 and dried over Na₂SO₄. After filtration the solvent was removed under reduced pressure to give a yellow oil which was purified by column chromatography (silica gel, iPrOAc/heptane) to give the title compound (1.05 g, 3.3 mmol; 25%) as yellow oil. MS: m/e=316.2 [M+H⁺].

1.2 2-Cyclohexyl-3-oxo-3-(2-oxo-cyclopentyl)-propionic acid ethyl ester

To a −78° C. cold solution of LDA (2 M solution in heptane/ethylbenzene/THF, 15.7 ml, 31 mmol) in THF (96 ml) under an argon atmosphere was added a solution of cyclopentanone (2.78 ml, 31 mmol; CAS Reg. No. 120-92-3) in THF (72 ml) within 25 min. The mixture was stirred for 2 h at −78° C. A solution of 3-benzotriazol-1-yl-2-cyclohexyl-3-oxo-propionic acid ethyl ester (9 g, 29 mmol) in THF (63 ml) was added and the solution was stirred at ambient temperature for 14 h. Ice water was added, the mixture was poured onto ice water/brine 1/1 and extracted two times with TBME. The combined extracts were washed with ice water/brine 1/1 and dried over Na₂SO₄. After filtration the solvent was removed under reduced pressure to give the title compound (8.8 g; quant.) which was used in the next step without further purification.

1.3 [2-(4-Chloro-phenyl)-2,4,5,6-tetrahydro-cyclopentapyrazol-3-yl]-cyclohexyl-acetic acid ethyl ester (4-Chloro-phenyl)-hydrazine (5.63 g, 31 mmol; CAS Reg. No. 1073-69-4) was added to a solution of 2-cyclohexyl-3-oxo-3-(2-oxo-cyclopentyl)-propionic acid ethyl ester (8.8 g, 31 mmol) in ethanol (200 ml). The reaction mixture was heated under reflux conditions for 6 h. The solvent was removed under reduced pressure. The residue was suspended in dichloromethane and filtered off. The filtrate was brought to dryness under reduced pressure to give a brown oil which was purified by column chromatography (silica gel, iPrOAc/heptane) to give the title compound (6.26 g, 16 mmol; 51%) as orange oil. MS: m/e=388.4 [M+H⁺].

1.4 2-[2-(4-Chloro-phenyl)-2,4,5,6-tetrahydro-cyclopentapyrazol-3-yl]-2-cyclohexyl-ethanol A solution of [2-(4-chloro-phenyl)-2,4,5,6-tetrahydro-cyclopentapyrazol-3-yl]-cyclohexyl-acetic acid ethyl ester (500 mg, 1.2 mmol) in THF (25 ml) was added within 20 min to an ice cold suspension of lithium aluminium hydride (66 mg, 1.7 mmol) in THF (25 ml). The solution was stirred at 0° C. for 45 min, filtered over Speedex and the filtrate was brought to dryness under reduced pressure. The residue was taken up in ice water/brine 1/1 and iPrOAc. The layers were separated and the aqueous layer was extracted one more time with iPrOAc. The combined extracts were dried over Na₂SO₄. After filtration the solvent was removed under reduced pressure to give the title compound (336 mg, 0.97 mmol; 79%) as yellow oil which was used in the next step without further purification. MS: m/e=345.2 [M+H⁺].

1.5 4-{2-[2-(4-Chloro-phenyl)-2,4,5,6-tetrahydro-cyclopentapyrazol-3-yl]-2-cyclohexyl-ethoxy}-3,5-dimethyl-benzoic acid methyl ester To a solution of 2-[2-(4-chloro-phenyl)-2,4,5,6-tetrahydro-cyclopentapyrazol-3-yl]-2-cyclohexyl-ethanol (100 mg, 290 umol) in THF (2 ml) was added 4-hydroxy-3,5-dimethyl-benzoic acid methyl ester (57 mg, 319 umol; CAS Reg. No. 34137-14-9) and tri-phenylphosphine (91 mg, 348 umol) at ambient temperature under an argon atmosphere. The mixture was cooled to 0° C., di-tert-butyl azodicarboxylate (80 mg, 348 umol) was added and the suspension was stirred for 48 h at ambient temperature. The solvent was removed under reduced pressure to give a solid which was purified by preparative HPLC on reversed phase eluting with a gradient of acetonitrile/water to obtain the title compound (19 mg, 37 umol; 13%) as yellow solid. MS: m/e=507.2 [M+H⁺].

Example 2

4-{2-[2-(4-Chloro-phenyl)-2,4,5,6-tetrahydro-cyclopentapyrazol-3-yl]-2-cyclohexyl-ethoxy}-3,5-dimethyl-benzoic acid

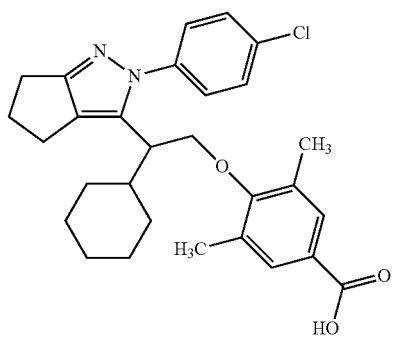

To a solution of 4-{2-[2-(4-chloro-phenyl)-2,4,5,6-tetrahydro-cyclopentapyrazol-3-yl]-2-cyclohexyl-ethoxy}-3,5-dimethyl-benzoic acid methyl ester (19 mg, 37 umol; example 1.5) in THF (0.7 ml) and MeOH (0.3 ml) was added a 1 N aqueous lithium hydroxide solution (450 ul, 450 umol) at ambient temperature under an argon atmosphere. The reaction mixture was stirred for 14 h at ambient temperature and poured onto ice water/1 N aqueous HCl solution 1/1. The mixture was extracted two times with iPrOAc. The combined extracts were washed with ice water/brine 1/1 and dried over $Na_2SO_4$. After filtration the solvent was removed under reduced pressure to obtain the title compound (25 mg; quant.) as colorless oil.

Example 3

4-{2-[2-(4-Chloro-phenyl)-2,4,5,6-tetrahydro-cyclopentapyrazol-3-yl]-2-cyclohexyl-ethoxy}-3-fluoro-benzonitrile

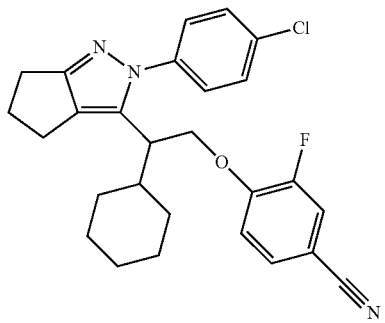

In analogy to the procedure described in example 1.5, 2-[2-(4-chloro-phenyl)-2,4,5,6-tetrahydro-cyclopentapyrazol-3-yl]-2-cyclohexyl-ethanol (example 1.4) was condensed with 3-fluoro-4-hydroxy-benzonitrile (CAS Reg. No. 405-04-9) in the presence of tri-phenylphosphine and di-tert-butyl azodicarboxylate in THF to give the title compound as white solid. MS: m/e=464.2 [M+H$^+$].

Example 4

2-[2-(4-Chloro-phenyl)-2,4,5,6-tetrahydro-cyclopentapyrazol-3-yl]-2,N-dicyclohexyl-acetamide

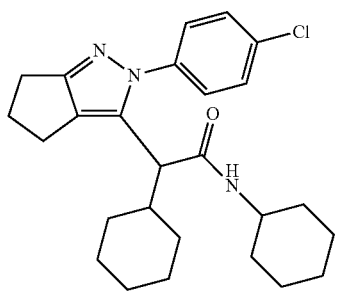

4.1 [2-(4-Chloro-phenyl)-2,4,5,6-tetrahydro-cyclopentapyrazol-3-yl]-cyclohexyl-acetic acid A solution of [2-(4-chloro-phenyl)-2,4,5,6-tetrahydro-cyclopentapyrazol-3-yl]-cyclohexyl-acetic acid ethyl ester (1 g, 2.6 mmol; example 1.3) in MeOH (56 ml) and 4 N aqueous NaOH (9.7 ml, 39 mmol) was stirred at ambient temperature for 14 h. The solvent was removed under reduced pressure, ice water/TBME 1/1 was added and the layers were separated. The aqueous layer was extracted one more time with TBME. The aqueous layer was acidified with 1 N aqueous HCl solution and extracted two times with iPrOAc. The combined extracts were washed with ice water/brine 1/1 and dried over $Na_2SO_4$. After filtration the solvent was removed under reduced pressure to give the title compound (570 mg, 1.59 mmol; 61%) as yellow oil which was sufficiently pure to be used in the next step. MS: m/e=359.2 [M+H$^+$].

4.2 [2-(4-Chloro-phenyl)-2,4,5,6-tetrahydro-cyclopentapyrazol-3-yl]-cyclohexyl-acetic acid pentafluorophenyl ester To a solution of [2-(4-chloro-phenyl)-2,4,5,6-tetrahydro-cyclopentapyrazol-3-yl]-cyclohexyl-acetic acid (300 mg, 836 umol) in DMF (3 ml) was added pyridine (70 ul, 920 umol) and pentafluorophenyl trifluoroacetate (290 ul, 1.7 mmol) at ambient temperature under an argon atmosphere. The reaction mixture was stirred at ambient temperature for 12 h, poured onto ice water/0.1 N HCl 1/1 and extracted two times with iPrOAc. The combined extracts were washed with ice water/sat. aqueous $NaHCO_3$ solution 1/1, ice water/brine 1/1 and dried over $Na_2SO_4$. After filtration the solvent was removed under reduced pressure to give [2-(4-chloro-phenyl)-2,4,5,6-tetrahydro-cyclopentapyrazol-3-yl]-cyclohexyl-acetic acid pentafluorophenyl ester as an orange oil (762 mg; quant.) which was directly used in the next reaction step without further purification.

4.3 2-[2-(4-Chloro-phenyl)-2,4,5,6-tetrahydro-cyclopentapyrazol-3-yl]-2,N-dicyclohexyl-acetamide To a suspension of [2-(4-chloro-phenyl)-2,4,5,6-tetrahydro-cyclopentapyrazol-3-yl]-cyclohexyl-acetic acid pentafluorophenyl ester (95 mg, 181 umol) in DMF (0.9 ml) was added cyclohexylamine (30 ul, 271 umol; CAS Reg. No. 108-91-8) and DMAP (66 mg, 543 umol) at ambient temperature under an argon atmosphere. The reaction mixture was stirred at ambient temperature for 30 h. The solvent was removed under reduced pressure to give a brown oil which was purified by preparative thin layer chromatography (silica gel, iPrOAc/heptane) to obtain the title compound (32 mg, 75 umol; 40%) as brown oil. MS: m/e=440.3 [M+H$^+$].

Example 5

2-(4-Chloro-phenyl)-3-{1-cyclohexyl-2-[2-fluoro-4-(2H-tetrazol-5-yl)-phenoxy]-ethyl}-2,4,5,6-tetrahydro-cyclopentapyrazole

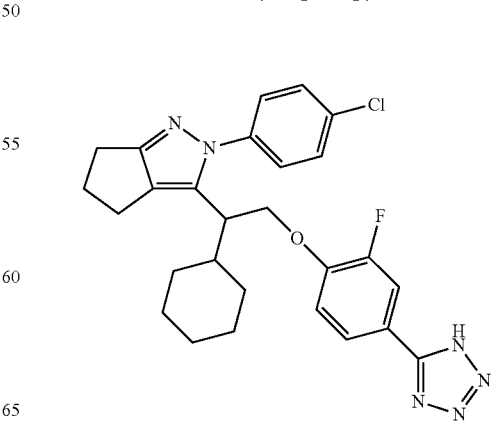

Sodium azide (14 mg, 215 umol) and triethylamine hydrochloride (29 mg, 215 umol) were added to a solution of 4-{2-[2-(4-chloro-phenyl)-2,4,5,6-tetrahydro-cyclopentapyrazol-3-yl]-2-cyclohexyl-ethoxy}-3-fluoro-benzonitrile (20 mg, 43 umol; example 3) in DMF (0.5 ml). The solution was stirred at 120° C. for 14 h, poured onto ice water/1 N aqueous HCl solution 1/1 and extracted two times with iPrOAc. The combined extracts were washed with ice water/brine 1/1 and dried over Na$_2$SO$_4$. The solvent was removed under reduced pressure to give a solid which was crystallized from heptane/dichloromethane to obtain the title compound (13 mg, 26 umol; 59%) as off-white solid. MS: m/e=507.2 [M+H$^+$].

Example 6

4-{2-[2-(4-Chloro-phenyl)-2,4,5,6-tetrahydro-cyclopentapyrazol-3-yl]-2-cyclohexyl-acetylamino}-3-fluoro-benzoic acid

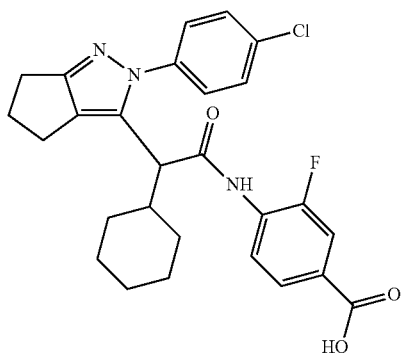

6.1 4-{2-[2-(4-Chloro-phenyl)-2,4,5,6-tetrahydro-cyclopentapyrazol-3-yl]-2-cyclohexyl-acetylamino}-3-fluoro-benzoic acid methyl ester In analogy to the procedure described in example 4.3, [2-(4-chloro-phenyl)-2,4,5,6-tetrahydro-cyclopentapyrazol-3-yl]-cyclohexyl-acetic acid pentafluorophenyl ester (example 4.2) was reacted with 4-amino-3-fluoro-benzoic acid methyl ester (CAS Reg. No. 185629-32-7) in the presence of DMAP in DMF to give the title compound as colorless oil. MS: m/e=510.2 [M+H$^+$].

6.2 4-{2-[2-(4-Chloro-phenyl)-2,4,5,6-tetrahydro-cyclopentapyrazol-3-yl]-2-cyclohexyl-acetylamino}-3-fluoro-benzoic acid In analogy to the procedure described in example 2,4-{2-[2-(4-chloro-phenyl)-2,4,5,6-tetrahydro-cyclopentapyrazol-3-yl]-2-cyclohexyl-acetylamino}-3-fluoro-benzoic acid methyl ester was hydrolysed using aqueous lithium hydroxide solution in THF and MeOH to give the title compound as brown solid. MS: m/e=494.2 [M−H$^-$].

Example 7

6-{2-[2-(4-Chloro-phenyl)-2,4,5,6-tetrahydro-cyclopentapyrazol-3-yl]-2-cyclohexyl-ethoxy}-nicotinic acid

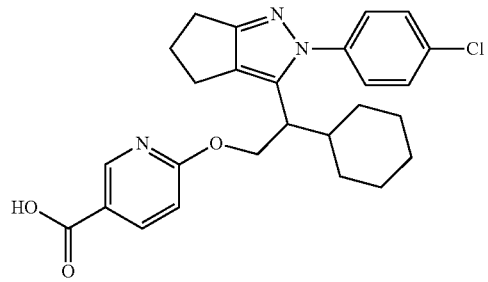

7.1 Methanesulfonic acid 2-[2-(4-chloro-phenyl)-2,4,5,6-tetrahydro-cyclopentapyrazol-3-yl]-2-cyclohexyl-ethyl ester To a solution of 2-[2-(4-chloro-phenyl)-2,4,5,6-tetrahydro-cyclopentapyrazol-3-yl]-2-cyclohexyl-ethanol (250 mg, 0.72 mmol; example 1.4) in dry dichloromethane (5 ml) was added triethylamine (0.32 ml, 1.19 mmol) at 25° C. Mesyl chloride (0.16 ml, 0.725 mmol) was added dropwise at 0° C. The reaction mixture was allowed to stir at 25° C. for 2 h, diluted with water (5 ml), and the aqueous layer was extracted with dichloromethane (3×10 ml). The combined organic layers were washed sequentially with ice water (10 ml), 10% aqueous NaHCO$_3$ solution (10 ml), brine (10 ml) and finally dried over Na$_2$SO$_4$. The solvent was removed under reduced pressure to give the title compound as light yellow oil (250 mg, 0.58 mmol; 81%), which was sufficiently pure to be used in the next reaction step.

7.2 6-{2-[2-(4-Chloro-phenyl)-2,4,5,6-tetrahydro-cyclopentapyrazol-3-yl]-2-cyclohexyl-ethoxy}-nicotinic acid methyl ester To a solution of methyl 6-hydroxynicotinate 4 (80 mg, 0.19 mmol; CAS Reg. No. 10128-91-3) in dry DMF (3 ml) was added dry K$_2$CO$_3$ (29 mg, 0.226 mmol) at 0° C. The reaction mixture was stirred for 15 minutes at 0° C. Methanesulfonic acid 2-[2-(4-chloro-phenyl)-2,4,5,6-tetrahydro-cyclopentapyrazol-3-yl]-2-cyclohexyl-ethyl ester (35 mg, 0.227 mmol) dissolved in dry DMF (1 ml) was added at 0° C. The reaction mixture was heated to 100° C. in a sealed tube for 12 h. 10% Aqueous citric acid solution (10 ml) and EtOAc (5 ml) were added to the reaction mixture. The layers were separated and the aqueous layer was extracted one more time with EtOAc (5 ml). The combined organic layers were washed with brine (5 ml) and dried over Na$_2$SO$_4$. The solvent was removed under reduced pressure to give a residue which was purified by column chromatography over silica gel (20% EtOAc/hexane) to give the title compound (60.2 mg, 0.12 mmol; 67%) as off-white solid.

7.3 6-{2-[2-(4-Chloro-phenyl)-2,4,5,6-tetrahydro-cyclopentapyrazol-3-yl]-2-cyclohexyl-ethoxy}-nicotinic acid In analogy to the procedure described in example 2, 6-{2-[2-(4-chloro-phenyl)-2,4,5,6-tetrahydro-cyclopentapyrazol-3-yl]-2-cyclohexyl-ethoxy}-nicotinic acid methyl ester was hydrolysed using aqueous sodium hydroxide solution in MeOH to give the title compound as off-white solid. MS: m/e=466.2 [M+H$^+$].

Example 8

4-{2-[2-(4-Chloro-phenyl)-2,4,5,6-tetrahydro-cyclopentapyrazol-3-yl]-2-cyclohexyl-ethylsulfanyl}-benzoic acid

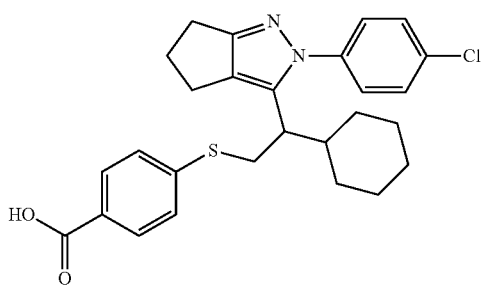

8.1 4-{2-[2-(4-Chloro-phenyl)-2,4,5,6-tetrahydro-cyclopentapyrazol-3-yl]-2-cyclohexyl-ethylsulfanyl}-benzoic acid methyl ester In analogy to the procedure described in example 7.2, methanesulfonic acid 2-[2-(4-chloro-phenyl)-2,4,5,6-tetrahydro-cyclopentapyrazol-3-yl]-2-cyclohexyl-ethyl ester (example 7.1) was reacted with 4-mercapto-benzoic acid methyl ester (CAS Reg. No. 6302-65-4) in the presence of $K_2CO_3$ in DMF to give the title compound as off-white solid.

8.2 4-{2-[2-(4-Chloro-phenyl)-2,4,5,6-tetrahydro-cyclopentapyrazol-3-yl]-2-cyclohexyl-ethylsulfanyl}-benzoic acid In analogy to the procedure described in example 2, 4-{2-[2-(4-chloro-phenyl)-2,4,5,6-tetrahydro-cyclopentapyrazol-3-yl]-2-cyclohexyl-ethylsulfanyl}-benzoic acid methyl ester was hydrolysed using aqueous sodium hydroxide solution in MeOH to give the title compound as off-white solid. MS: m/e=481.4 [M+H$^+$].

Example 9

2-(4-{2-[2-(4-Chloro-phenyl)-2,4,5,6,7,8-hexahydro-cycloheptapyrazol-3-yl]-2-cyclohexyl-acetylamino}-3-fluoro-phenoxy)-2-methyl-propionic acid ethyl ester

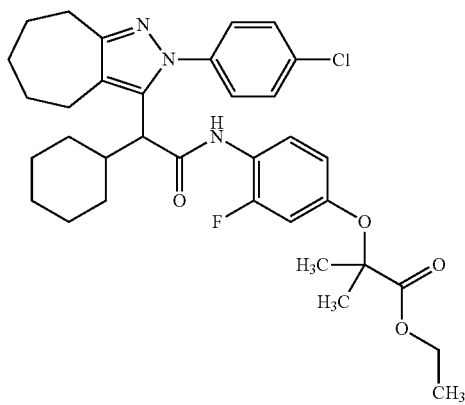

9.1 2-Cyclohexyl-3-oxo-3-(2-oxo-cycloheptyl)-propionic acid ethyl ester

In analogy to the procedure described in example 1.2, 3-benzotriazol-1-yl-2-cyclohexyl-3-oxo-propionic acid ethyl ester (example 1.1) was treated with LDA and subsequently reacted with cycloheptanone (CAS Reg. No. 502-42-1) in THF to give the title compound as yellow oil.

9.2 [2-(4-Chloro-phenyl)-2,4,5,6,7,8-hexahydro-cycloheptapyrazol-3-yl]-cyclohexyl-acetic acid ethyl ester In analogy to the procedure described in example 1.3, 2-cyclohexyl-3-oxo-3-(2-oxo-cycloheptyl)-propionic acid ethyl ester was condensed with (4-chloro-phenyl)-hydrazine (CAS Reg. No. 1073-69-4) in ethanol to give the title compound as orange oil. MS: m/e=415.3 [M+H$^+$].

9.3 [2-(4-Chloro-phenyl)-2,4,5,6,7,8-hexahydro-cycloheptapyrazol-3-yl]-cyclohexyl-acetic acid A solution of [2-(4-chloro-phenyl)-2,4,5,6,7,8-hexahydro-cycloheptapyrazol-3-yl]-cyclohexyl-acetic acid ethyl ester (337 mg, 812 umol) in MeOH (19 ml) and 4 N aqueous NaOH (3.05 ml, 12.2 umol) was heated for 14 h under reflux conditions. The solvent was removed under reduced pressure, ice water/2 N aqueous HCl solution/iPrOAc 1/1/2 was added and the layers were separated. The aqueous layer was extracted one more time with iPrOAc. The combined extracts were washed with ice water/brine 1/1 and dried over $Na_2SO_4$. After filtration the solvent was removed under reduced pressure to give the title compound (284 mg, 734 umol; 90%) as off-white solid which was sufficiently pure to be used in the next step. MS: m/e=387.2 [M+H

9.4 2-(3-Fluoro-4-nitro-phenoxy)-2-methyl-propionic acid ethyl ester

Potassium carbonate (3.96 g, 29 mmol) and 2-bromo-2-methylpropanoic acid ethyl ester (4.47 g, 23 mmol; CAS Reg. No. 600-00-0) were added to a solution of 3-fluoro-4-nitrophenol (3 g, 19 mmol; CAS Reg. No. 394-41-2) in DMSO (50 ml). The mixture was stirred for 18 h at 100° C. 10% aqueous citric acid and EtOAc were added and the layers were separated. The organic layer was washed with brine and dried over $MgSO_4$. The solid was filtered off and the filtrate concentrated under reduced pressure. The residue was purified by column chromatography (silica gel, EtOAc/heptane) to obtain the title compound (1.19 g, 4.4 mmol; 23%) as yellow oil.

9.5 2-(4-Amino-3-fluoro-phenoxy)-2-methyl-propionic acid ethyl ester

10% Palladium on carbon (200 mg) was added to a solution of 2-(3-fluoro-4-nitro-phenoxy)-2-methyl-propionic acid ethyl ester (1.15 g, 4 mmol) in ethanol (20 ml). The suspension was hydrogenated at a hydrogen gas pressure of 1.7 bar for 8 h at ambient temperature. Ethyl acetate was added (100 ml), the solid was filtered off and the filtrate was brought to dryness under reduced pressure to give the title compound (1.23 g, quant.) which was used in the next step without further purification.

9.6 2-(4-{2-[2-(4-Chloro-phenyl)-2,4,5,6,7,8-hexahydro-cycloheptapyrazol-3-yl]-2-cyclohexyl-acetylamino}-3-fluoro-phenoxy)-2-methyl-propionic acid ethyl ester A solution of [2-(4-chloro-phenyl)-2,4,5,6,7,8-hexahydro-cycloheptapyrazol-3-yl]-cyclohexyl-acetic acid (40 mg, 103 umol) in thionyl chloride (2 ml) was heated under reflux conditions for 45 min. The solvent was removed under reduced pressure and the resulting crude [2-(4-chloro-phenyl)-2,4,5,6,7,8-hexahydro-cycloheptapyrazol-3-yl]-cyclohexyl-acetyl chloride was dissolved in CH$_2$Cl$_2$ (1 ml) and added to a solution of 2-(4-amino-3-fluoro-phenoxy)-2-methyl-propionic acid ethyl ester (37 mg, 155 umol) and DMAP (38 mg, 310 umol) in CH$_2$Cl$_2$ (1 ml). The reaction mixture was stirred at ambient temperature for 14 h. Ice water/brine 1/1 was added and the mixture was extracted two times with iPrOAc. The combined extracts were washed with ice water/brine 1/1 and dried over Na$_2$SO$_4$. After filtration the solvent was removed under reduced pressure to give a brown oil which was purified by preparative HPLC on reversed phase eluting with a gradient of acetonitrile/water to obtain the title compound (15 mg, 25 umol; 24%) as brown solid. MS: m/e=610.3 [M+H$^+$].

Example 10

2-(4-{2-[2-(4-Chloro-phenyl)-2,4,5,6,7,8-hexahydro-cycloheptapyrazol-3-yl]-2-cyclohexyl-acetylamino}-3-fluoro-phenoxy)-2-methyl-propionic acid

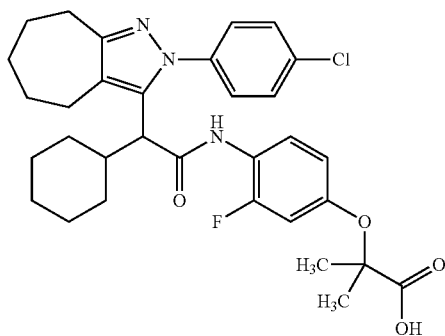

In analogy to the procedure described in example 2,2-(4-{2-[2-(4-chloro-phenyl)-2,4,5,6,7,8-hexahydro-cycloheptapyrazol-3-yl]-2-cyclohexyl-acetylamino}-3-fluoro-phenoxy)-2-methyl-propionic acid ethyl ester (example 9.6) was hydrolysed using aqueous lithium hydroxide solution in THF and MeOH to give the title compound as red solid. MS: m/e=582.4 [M+H$^+$].

Example 11

2-[2-(4-Chloro-phenyl)-2,4,5,6,7,8-hexahydro-cyclo-heptapyrazol-3-yl]-2,N-dicyclohexyl-acetamide

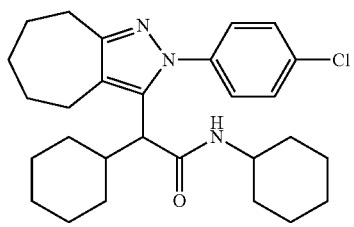

In analogy to the procedure described in example 9.6, [2-(4-chloro-phenyl)-2,4,5,6,7,8-hexahydro-cycloheptapyrazol-3-yl]-cyclohexyl-acetic acid (example 9.3) was converted into the corresponding acid chloride with thionyl chloride which subsequently reacted with cyclohexylamine (CAS Reg. No. 108-91-8) in the presence of DMAP to give the title compound as off-white solid. MS: m/e=468.3 [M+H$^+$].

Example 12

4-{2-[2-(4-Chloro-phenyl)-2,4,5,6,7,8-hexahydro-cycloheptapyrazol-3-yl]-2-cyclohexyl-acetylamino}-3-fluoro-benzoic acid methyl ester

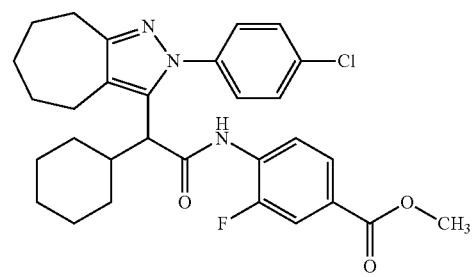

In analogy to the procedure described in example 9.6, [2-(4-chloro-phenyl)-2,4,5,6,7,8-hexahydro-cycloheptapyrazol-3-yl]-cyclohexyl-acetic acid (example 9.3) was converted into the corresponding acid chloride with thionyl chloride which subsequently reacted with 4-amino-3-fluoro-benzoic acid methyl ester (CAS Reg. No. 185629-32-7) in the presence of DMAP to give the title compound as off-white solid. MS: m/e=538.3 [M+H$^+$].

Example 13

4-{2-[2-(4-Chloro-phenyl)-2,4,5,6,7,8-hexahydro-cycloheptapyrazol-3-yl]-2-cyclohexyl-acetylamino}-3-fluoro-benzoic acid

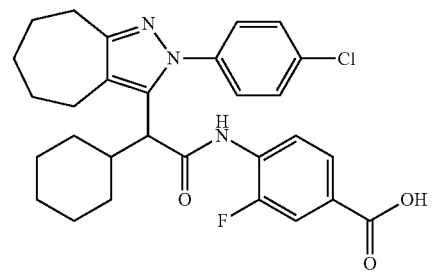

In analogy to the procedure described in example 2, 4-{2-[2-(4-chloro-phenyl)-2,4,5,6,7,8-hexahydro-cycloheptapyrazol-3-yl]-2-cyclohexyl-acetylamino}-3-fluoro-benzoic acid methyl ester (example 12) was hydrolysed using aqueous lithium hydroxide solution in THF and MeOH to give the title compound as white solid. MS: m/e=524.2 [M+H$^+$].

Example 14

4-{2-[2-(4-Chloro-phenyl)-2,4,5,6,7,8-hexahydro-cycloheptapyrazol-3-yl]-2-cyclohexyl-ethoxy}-3-fluoro-benzonitrile

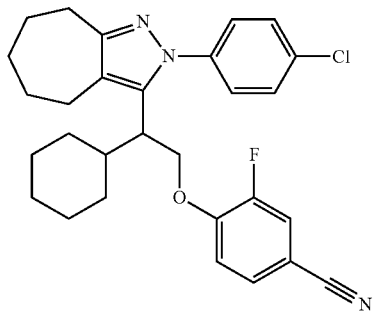

14.1 2-[2-(4-Chloro-phenyl)-2,4,5,6,7,8-hexahydro-cycloheptapyrazol-3-yl]-2-cyclohexyl-ethanol Borane-tetrahydrofuran complex (920 ul, 920 umol; 1 M solution in THF) was added to an ice cold solution of [2-(4-chloro-phenyl)-2,4,5,6,7,8-hexahydro-cycloheptapyrazol-3-yl]-cyclohexyl-acetic acid (143 mg, 370 umol; example 9.3) in THF (1.5 ml). The solution was stirred at ambient temperature for 14 h and cooled to 0° C. Methanol (1.5 ml) and water (1.5 ml) were added and the mixture was extracted two times with iPrOAc. The combined extracts were washed with brine and dried over $Na_2SO_4$. The solvent was removed under reduced pressure, the residue was dissolved in methanol (4.5 ml) and heated under reflux conditions for 30 min. The solvent was removed under reduced pressure and the residue purified by preparative thin layer chromatography (silica gel, iPrOAc/heptane) to obtain the title compound (70 mg, 188 umol; 51%) as colorless oil. MS: m/e=373.2 [M+H$^+$].

14.2 4-{2-[2-(4-Chloro-phenyl)-2,4,5,6,7,8-hexahydro-cycloheptapyrazol-3-yl]-2-cyclohexyl-ethoxy}-3-fluoro-benzonitrile In analogy to the procedure described in example 1.5, 2-[2-(4-chloro-phenyl)-2,4,5,6,7,8-hexahydro-cycloheptapyrazol-3-yl]-2-cyclohexyl-ethanol was condensed with 3-fluoro-4-hydroxy-benzonitrile (CAS Reg. No. 405-04-9) in the presence of tri-phenylphosphine and di-tert-butyl azodicarboxylate in THF to give the title compound as off-white solid. MS: m/e=492.2 [M+H$^+$].

Example 15

4-{2-[2-(4-Chloro-phenyl)-2,4,5,6,7,8-hexahydro-cycloheptapyrazol-3-yl]-2-cyclohexyl-ethoxy}-3,5-dimethyl-benzoic acid

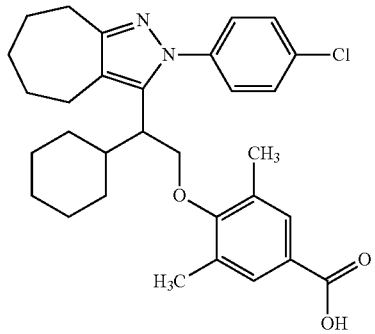

15.1 4-{2-[2-(4-Chloro-phenyl)-2,4,5,6,7,8-hexahydro-cycloheptapyrazol-3-yl]-2-cyclohexyl-ethoxy}-3,5-dimethyl-benzoic acid methyl ester In analogy to the procedure described in example 1.5, 2-[2-(4-chloro-phenyl)-2,4,5,6,7,8-hexahydro-cycloheptapyrazol-3-yl]-2-cyclohexyl-ethanol was condensed with 4-hydroxy-3,5-dimethyl-benzoic acid methyl ester (CAS Reg. No. 34137-14-9) in the presence of tri-phenylphosphine and di-tert-butyl azodicarboxylate in THF to give the title compound as white solid. MS: m/e=535.2 [M+H$^+$].

15.2 4-{2-[2-(4-Chloro-phenyl)-2,4,5,6,7,8-hexahydro-cycloheptapyrazol-3-yl]-2-cyclohexyl-ethoxy}-3,5-dimethyl-benzoic acid In analogy to the procedure described in example 2, 4-{2-[2-(4-chloro-phenyl)-2,4,5,6,7,8-hexahydro-cycloheptapyrazol-3-yl]-2-cyclohexyl-ethoxy}-3,5-dimethyl-benzoic acid methyl ester was hydrolysed using aqueous lithium hydroxide solution in THF and MeOH to give the title compound as off-white solid. MS: m/e=507.2 [M+H$^+$].

Example 16

2-(4-Chloro-phenyl)-3-{1-cyclohexyl-2-[2-fluoro-4-(1H-tetrazol-5-yl)-phenoxy]-ethyl}-2,4,5,6,7,8-hexahydro-cycloheptapyrazole

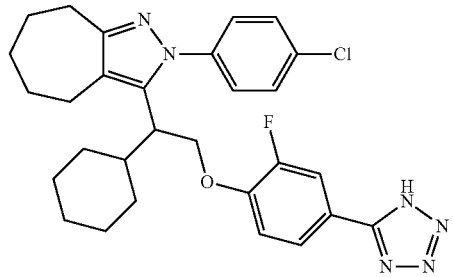

In analogy to the procedure described in example 5, 4-{2-[2-(4-chloro-phenyl)-2,4,5,6,7,8-hexahydro-cycloheptapyrazol-3-yl]-2-cyclohexyl-ethoxy}-3-fluoro-benzonitrile (example 14.2) was treated with sodium azide and triethylamine hydrochloride in DMF to give the title compound as white solid. MS: m/e=535.7 [M+H$^+$].

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
| --- | --- |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
| --- | --- |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesiumstearate and the flavouring additives and filled into sachets.

The invention claimed is:

1. A compound of the formula I,

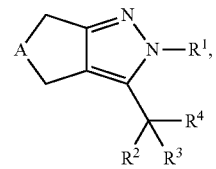

wherein

A is —CH$_2$— or —(CH$_2$)$_3$—,

R$^1$ is a ring selected from phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;

R$^2$ is selected from the group consisting of hydrogen, methyl, ethyl, hydroxy, methoxy, fluoro, fluoromethyl, difluoromethyl and trifluoromethyl;

R$^3$ is selected from the group consisting of:

unsubstituted cycloalkyl or cycloalkyl substituted 1 to 4 groups independently selected from methyl and fluoro;

lower cycloalkylalkyl;

unsubstituted phenyl;

phenyl substituted with 1 to 3 substituents independently selected from the group consisting of lower alkyl, halogen, lower halogenalkyl, hydroxy, lower alkoxy, lower halogenalkoxy and cyano; and heterocyclyl;

R$^4$ is selected from the group consisting of —C(O)—NH—R$^5$,

—CR$^7$R$^8$—OR$^6$, —O—(CR$^7$R$^8$)$_n$—R$^6$;

—CR$^7$R$^8$—SR$^6$, —CR$^7$R$^8$—SO—R$^6$, —CR$^7$R$^8$—SO$_2$—R$^6$,

—CR$^7$R$^8$—NH—R$^6$; —CH=CH—R$^6$ and —(CH$_2$)$_2$—R$^6$, wherein n is 0 or 1, R$^5$ is selected from the group consisting of:

lower alkyl; cycloalkyl;

lower cycloalkylalkyl;

cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;

unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl and tetrazolyl;
$R^6$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
heterocyclyl;
unsubstituted pyridyl;
pyridyl substituted by carboxyl, lower alkoxycarbonyl or tetrazolyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and
$R^7$ and $R^8$ independently are selected from the group consisting of hydrogen, lower alkyl and lower halogenalkyl, or
$R^7$ and $R^8$ together with the carbon atom to which they are attached form a cycloalkyl or alkoxycycloalkyl ring;
or a pharmaceutically acceptable salt thereof.

2. A compound according to claim 1, wherein $R^1$ is a phenyl ring, said ring being unsubstituted or substituted with 1 to 3 substituents independently selected from the group consisting of lower alkyl, halogen, lower halogenalkyl, hydroxy, lower alkoxy, lower halogenalkoxy and cyano.

3. A compound according to claim 1, wherein $R^1$ is phenyl or phenyl substituted with halogen.

4. A compound according to claim 1, wherein $R^2$ is hydrogen.

5. A compound according to claim 1, wherein $R^3$ is cycloalkyl.

6. A compound according to claim 1, wherein $R^4$ is selected from the group consisting of —C(O)—NH—$R^5$, —C$R^7R^8$—O$R^6$ and —C$R^7R^8$—S$R^6$, wherein
$R^5$ is selected from the group consisting of
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
unsubstituted phenyl;
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl or tetrazolyl;
$R^6$ is selected from the group consisting of
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
heterocyclyl;
unsubstituted pyridyl;
pyridyl substituted by carboxyl, lower alkoxycarbonyl or tetrazolyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and
$R^7$ and $R^8$ independently are selected from the group consisting of hydrogen, lower alkyl and lower halogenalkyl, or
$R^7$ and $R^8$ together with the carbon atom to which they are attached form a cycloalkyl or alkoxycycloalkyl ring.

7. A compound according to claim 1, wherein $R^4$ is —C(O)—NH—$R^5$; and
$R^5$ is selected from the group consisting of:
lower alkyl;
cycloalkyl;
lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
unsubstituted phenyl;
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
unsubstituted pyridyl; and
pyridyl substituted by a group selected from the group consisting of carboxyl, lower alkoxycarbonyl and tetrazolyl.

8. A compound according to claim 7, wherein $R^5$ is selected from the group consisting of: cycloalkyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl.

9. A compound according to claim 7, wherein $R^5$ is selected from the group consisting of cycloalkyl and phenyl substituted with 1 to 3 substituents independently selected from the group consisting of lower alkyl, halogen, carboxyl, tetrazolyl, lower alkoxycarbonyl, lower carboxylalkoxy, lower alkoxycarbonylalkoxy and cyano.

10. A compound according to claim 7, wherein $R^5$ is cycloalkyl or phenyl substituted with 1 to 3 substituents independently selected from the group consisting of halogen, carboxyl, lower alkoxycarbonyl, lower carboxylalkoxy and lower alkoxycarbonylalkoxy.

11. A compound according to claim 1, wherein $R^4$ is —$CR^7R^8$—$OR^6$ and wherein
$R^6$ is selected from the group consisting of:
lower alkyl;
cycloalkyl; lower cycloalkylalkyl;
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy;
heterocyclyl;
unsubstituted pyridyl;
pyridyl substituted by carboxyl, lower alkoxycarbonyl or tetrazolyl;
unsubstituted phenyl; and
phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl; and
$R^7$ and $R^8$ are hydrogen.

12. A compound according to claim 11, wherein $R^6$ is selected from the group consisting of cycloalkyl and phenyl substituted with 1 to 3 substituents independently selected from the group consisting of lower alkyl, halogen, carboxyl, tetrazolyl, lower alkoxycarbonyl, lower carboxylalkoxy, lower alkoxycarbonylalkoxy and cyano.

13. A compound according to claim 1, wherein A is —$CH_2$—.

14. A compound according to claim 1, wherein A is —$(CH_2)_3$—.

15. A compound according to claim 1, selected from the group consisting of:
4-{2-[2-(4-chloro-phenyl)-2,4,5,6-tetrahydro-cyclopentapyrazol-3-yl]-2-cyclohexyl-ethoxy}-3,5-dimethyl-benzoic acid methyl ester,
4-{2-[2-(4-chloro-phenyl)-2,4,5,6-tetrahydro-cyclopentapyrazol-3-yl]-2-cyclohexyl-ethoxy}-3,5-dimethyl-benzoic acid,
4-{2-[2-(4-chloro-phenyl)-2,4,5,6-tetrahydro-cyclopentapyrazol-3-yl]-2-cyclohexyl-ethoxy}-3-fluoro-benzonitrile,
2-[2-(4-chloro-phenyl)-2,4,5,6-tetrahydro-cyclopentapyrazol-3-yl]-2,N-dicyclohexyl-acetamide,
2-(4-chloro-phenyl)-3-{1-cyclohexyl-2-[2-fluoro-4-(2H-tetrazol-5-yl)-phenoxy]-ethyl}-2,4,5,6-tetrahydro-cyclopentapyrazole,
4-{2-[2-(4-chloro-phenyl)-2,4,5,6-tetrahydro-cyclopentapyrazol-3-yl]-2-cyclohexyl-acetylamino}-3-fluoro-benzoic acid,
6-{2-[2-(4-chloro-phenyl)-2,4,5,6-tetrahydro-cyclopentapyrazol-3-yl]-2-cyclohexyl-ethoxy}-nicotinic acid,
4-{2-[2-(4-chloro-phenyl)-2,4,5,6-tetrahydro-cyclopentapyrazol-3-yl]-2-cyclohexyl-ethylsulfanyl}-benzoic acid,
2-(4-{2-[2-(4-chloro-phenyl)-2,4,5,6,7,8-hexahydro-cycloheptapyrazol-3-yl]-2-cyclohexyl-acetylamino}-3-fluoro-phenoxy)-2-methyl-propionic acid ethyl ester,
2-(4-{2-[2-(4-chloro-phenyl)-2,4,5,6,7,8-hexahydro-cycloheptapyrazol-3-yl]-2-cyclohexyl-acetylamino}-3-fluoro-phenoxy)-2-methyl-propionic acid,
and pharmaceutically-acceptable salts thereof.

16. A pharmaceutical composition comprising a compound according to claim 1 and a pharmaceutically acceptable carrier and/or adjuvant.

17. A compound according to claim 1, selected from the group consisting of:
2-[2-(4-chloro-phenyl)-2,4,5,6,7,8-hexahydro-cycloheptapyrazol-3-yl]-2,N-dicyclohexyl-acetamide,
4-{2-[2-(4-chloro-phenyl)-2,4,5,6,7,8-hexahydro-cycloheptapyrazol-3-yl]-2-cyclohexyl-acetylamino}-3-fluoro-benzoic acid methyl ester,
4-{2-[2-(4-chloro-phenyl)-2,4,5,6,7,8-hexahydro-cycloheptapyrazol-3-yl]-2-cyclohexyl-acetylamino}-3-fluoro-benzoic acid,
4-{2-[2-(4-chloro-phenyl)-2,4,5,6,7,8-hexahydro-cycloheptapyrazol-3-yl]-2-cyclohexyl-ethoxy}-3-fluoro-benzonitrile,
4-{2-[2-(4-chloro-phenyl)-2,4,5,6,7,8-hexahydro-cycloheptapyrazol-3-yl]-2-cyclohexyl-ethoxy}-3,5-dimethyl-benzoic acid,
2-(4-chloro-phenyl)-3-{1-cyclohexyl-2-[2-fluoro-4-(1H-tetrazol-5-yl)-phenoxy]-ethyl}-2,4,5,6,7,8-hexahydro-cycloheptapyrazole,
and pharmaceutically acceptable salts thereof.

\* \* \* \* \*